United States Patent
Hareland et al.

(10) Patent No.: US 9,844,675 B2
(45) Date of Patent: Dec. 19, 2017

(54) ENABLING AND DISABLING ANTI-TACHYARRHYTHMIA PACING IN A CONCOMITANT MEDICAL DEVICE SYSTEM

(71) Applicant: Medtronic, Inc., Minneapolis, MN (US)

(72) Inventors: Scott A. Hareland, Lino Lakes, MN (US); James K. Carney, Falcon Heights, MN (US); James D. Reinke, Maple Grove, MN (US); Jon D. Schell, Shoreview, MN (US); Barbara J. Schmid, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/143,038

(22) Filed: Apr. 29, 2016

(65) Prior Publication Data
US 2017/0312514 A1 Nov. 2, 2017

(51) Int. Cl.
*A61N 1/37* (2006.01)
*A61N 1/362* (2006.01)
*A61N 1/372* (2006.01)
*A61N 1/39* (2006.01)
*A61N 1/375* (2006.01)

(52) U.S. Cl.
CPC ......... *A61N 1/3621* (2013.01); *A61N 1/3756* (2013.01); *A61N 1/37252* (2013.01); *A61N 1/3962* (2013.01); *A61N 1/3987* (2013.01)

(58) Field of Classification Search
CPC . A61N 1/3621; A61N 1/3962; A61N 1/37288
See application file for complete search history.

(56) References Cited

U.S. PATENT DOCUMENTS

| | | |
|---|---|---|
| 4,494,950 A | 1/1985 | Fischell |
| 4,895,151 A | 1/1990 | Grevis et al. |
| 5,117,824 A | 6/1992 | Keimel et al. |
| 5,354,316 A | 10/1994 | Keimel |
| 5,456,692 A | 10/1995 | Smith, Jr. et al. |
| 5,507,782 A | 4/1996 | Kieval et al. |
| 5,545,186 A | 8/1996 | Olson et al. |
| 5,683,432 A | 11/1997 | Goedeke et al. |
| 5,725,559 A | 3/1998 | Alt et al. |
| 5,755,736 A | 5/1998 | Gillberg et al. |
| 6,393,316 B1 | 5/2002 | Gillberg et al. |

(Continued)

OTHER PUBLICATIONS

Demmer, "Multi-Device Implantable Medical Device System and Programming Methods", U.S. Appl. No. 14/601,915, filed Jan. 21, 2015, 71 pages.

(Continued)

*Primary Examiner* — Michael Kahelin

(57) ABSTRACT

An implantable medical device comprising a signal generator configured to generate and deliver anti-tachyarrhythmia pacing (ATP) to a heart of a patient and processing circuitry. The processing circuitry is configured to detect an enable event, responsive to detecting the enable event, enable the delivery of ATP by the signal generator, detect a disable event indicating that another implantable medical device cannot be relied upon to deliver an anti-tachyarrhythmia shock, and responsive to detecting the disable event, disable delivery of ATP.

11 Claims, 15 Drawing Sheets

(56) References Cited

U.S. PATENT DOCUMENTS

| | | |
|---|---|---|
| 6,442,433 B1 | 8/2002 | Linberg |
| 6,471,645 B1 | 10/2002 | Warkentin et al. |
| 6,599,250 B2 | 7/2003 | Webb et al. |
| 6,647,434 B1 | 11/2003 | Kamepalli |
| 6,892,094 B2 | 5/2005 | Ousdigian et al. |
| 7,031,771 B2 | 4/2006 | Brown et al. |
| 7,181,505 B2 | 2/2007 | Haller et al. |
| 7,565,197 B2 | 7/2009 | Haubrich et al. |
| 7,583,995 B2 | 9/2009 | Sanders |
| 7,720,543 B2 | 5/2010 | Dudding et al. |
| 7,742,816 B2 | 6/2010 | Masoud et al. |
| 7,949,404 B2 | 5/2011 | Hill |
| 8,036,746 B2 | 10/2011 | Sanders |
| 8,102,789 B2 | 1/2012 | Rosar et al. |
| 8,160,684 B2 | 4/2012 | Ghanem et al. |
| 8,352,025 B2 | 1/2013 | Jacobson |
| 8,352,038 B2 | 1/2013 | Mao et al. |
| 8,433,409 B2 | 4/2013 | Johnson et al. |
| 8,437,842 B2 | 5/2013 | Zhang et al. |
| 8,457,742 B2 | 6/2013 | Jacobson |
| 8,532,785 B1 | 9/2013 | Crutchfield et al. |
| 8,541,131 B2 | 9/2013 | Lund et al. |
| 8,744,572 B1 | 6/2014 | Greenhut et al. |
| 8,923,963 B2 | 12/2014 | Bonner et al. |
| 9,278,229 B1 | 3/2016 | Reinke et al. |
| 2002/0013613 A1 | 1/2002 | Haller et al. |
| 2004/0220624 A1* | 11/2004 | Ritscher ............... A61N 1/3622 607/4 |
| 2006/0135999 A1 | 6/2006 | Bodner et al. |
| 2006/0241701 A1* | 10/2006 | Markowitz ............ A61N 1/025 607/5 |
| 2007/0299480 A1 | 12/2007 | Hill |
| 2009/0138058 A1 | 5/2009 | Cooke et al. |
| 2009/0299438 A1 | 12/2009 | Nolan et al. |
| 2012/0016305 A1 | 1/2012 | Jollota et al. |
| 2012/0303078 A1 | 11/2012 | Li et al. |
| 2013/0035748 A1 | 2/2013 | Bonner et al. |
| 2014/0121719 A1 | 5/2014 | Bonner et al. |
| 2014/0121720 A1 | 5/2014 | Bonner et al. |
| 2014/0214104 A1 | 7/2014 | Greenhut et al. |
| 2014/0330326 A1 | 11/2014 | Thompson-Nauman et al. |
| 2014/0337922 A1 | 11/2014 | Sievert et al. |
| 2015/0290467 A1* | 10/2015 | Ludwig ................ A61N 1/3962 607/4 |
| 2015/0305641 A1 | 10/2015 | Stadler et al. |
| 2015/0360041 A1 | 12/2015 | Stahmann et al. |

OTHER PUBLICATIONS

Mondesert, et al., "Combination of a leadless pacemaker and subcutaneous defibrillator: First in-human report," Heart Rhythm Case Reports, vol. 1, No. 6, Nov. 2015, p. 469-471.

(PCT/US2017/029540) PCT Notification of Transmittal of the International Search Report and the Written Opinion of the International Searching Authority, dated Jun. 28, 2017, 11 pages.

* cited by examiner

ENABLING AND DISABLING ANTI-TACHYARRHYTHMIA PACING IN A CONCOMITANT MEDICAL DEVICE SYSTEM

TECHNICAL FIELD

This disclosure relates generally to medical devices and, more particularly, to medical devices, medical device systems, and methods for treating cardiac arrhythmias.

BACKGROUND

Implantable cardioverter defibrillators (ICDs) and implantable artificial pacemakers may provide cardiac pacing therapy to a patient's heart when the natural pacemaker and/or conduction system of the heart fails to provide synchronized atrial and ventricular contractions at rates and intervals sufficient to sustain healthy patient function. Such antibradycardial pacing may provide relief from symptoms, or even life support, for a patient. Cardiac pacing may also provide electrical overdrive stimulation, e.g., anti-tachyarrhythmia pacing (ATP) therapy, to suppress or convert tachyarrhythmias, again supplying relief from symptoms and preventing or terminating arrhythmias that could lead to sudden cardiac death.

SUMMARY

Some extracardiovascular defibrillators, such as subcutaneous ICDs, may have limited capabilities to provide anti-tachyarrhythmia pacing (ATP) therapies to terminate some types of tachyarrhythmia episodes. In such situations, an additional pacing device may be used that is capable of delivering ATP therapy. The systems and methods described herein include techniques that may be used to enable and disable delivery of ATP therapy in such a pacing device, depending on whether a device capable of delivering an anti-tachyarrhythmia shock is considered to be available.

In one example, this disclosure is directed to a method comprising detecting, by an implantable medical device configured to deliver ATP to a heart of a patient, an enable event. The method further comprises, responsive to detecting the enable event, enabling, by the implantable medical device, the delivery of ATP. The method further comprises detecting, by the implantable medical device, a disable event indicating that another implantable medical device cannot be relied upon to deliver an anti-tachyarrhythmia shock. The method further comprises, responsive to detecting the disable event, disabling, by the implantable medical device, delivery of ATP.

In another example, this disclosure is directed to an implantable medical device comprising signal generation circuitry configured to generate and deliver ATP to a heart of a patient and processing circuitry. The processing circuitry is configured to detect an enable event, responsive to detecting the enable event, enable the delivery of ATP by signal generation circuitry, detect a disable event indicating that another implantable medical device cannot be relied upon to deliver an anti-tachyarrhythmia shock and responsive to detecting the disable event, disable delivery of ATP.

In a further example, this disclosure is directed to a non-transitory computer-readable storage medium encoded with instructions that, when executed by processing circuitry an implantable medical device configured to deliver ATP to a heart of a patient, cause the processor to detect an enable event, responsive to detecting the enable event, enable the delivery of ATP by the implantable medical device, detect a disable event indicating that another implantable medical device cannot be relied upon to deliver an anti-tachyarrhythmia shock, and responsive to detecting the disable event, disable delivery of ATP.

In a further example, this disclosure is directed to a system comprising an extracardiovascular medical device configured for extracardiovascular implantation within a patient and configured to deliver an anti-tachyarrhythmia shock, and an intracardiac pacing device. The intracardiac pacing device comprises a housing configured for implantation within a heart of the patient, a plurality of electrodes configured for implantation in the heart, signal generation circuitry within the housing, signal generation circuitry configured to deliver ATP to the heart via the plurality of electrodes, communication circuitry within the housing and configured to receive enable signals from an external device via wireless communication or telemetry, and processing circuitry within the housing. The processing circuitry is configured to detect receipt of an enable signal from the external device, responsive to detecting the receipt of the enable signal, enable the delivery of ATP by signal generation circuitry, responsive to detecting receipt of the enable signal, start a timer, responsive to detecting receipt of each of one or more subsequent enable signals, restart the timer, and responsive to detecting expiration of the timer, disable delivery of ATP.

In a further example, this disclosure is directed to a method comprising evaluating a medical device system implanted in a patient, the medical device system including an implanted pacing device and an implanted cardiac defibrillator. The method further comprises performing an assessment of the implanted cardiac defibrillator to determine a time period during which the implanted cardiac defibrillator is expected to continue operate properly. The method further comprises sending an enable command to the implanted pacing device, the enable command including information derived from the time period during which the implanted cardiac defibrillator is expected to operate properly.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

In general, this disclosure describes subject matter relating to the delivery of anti-tachyarrhythmia pacing (ATP) therapies in a concomitant cardiac medical device system. In accordance with one or more aspects of the present disclosure, techniques are described that may help ensure that a pacing device provide ATP therapy, in some examples, only when another device capable of delivering an anti-tachyarrhythmia shock is available. In the following description, references are made to illustrative examples. It is understood that other examples may be utilized without departing from the scope of the disclosure.

Figure 1:
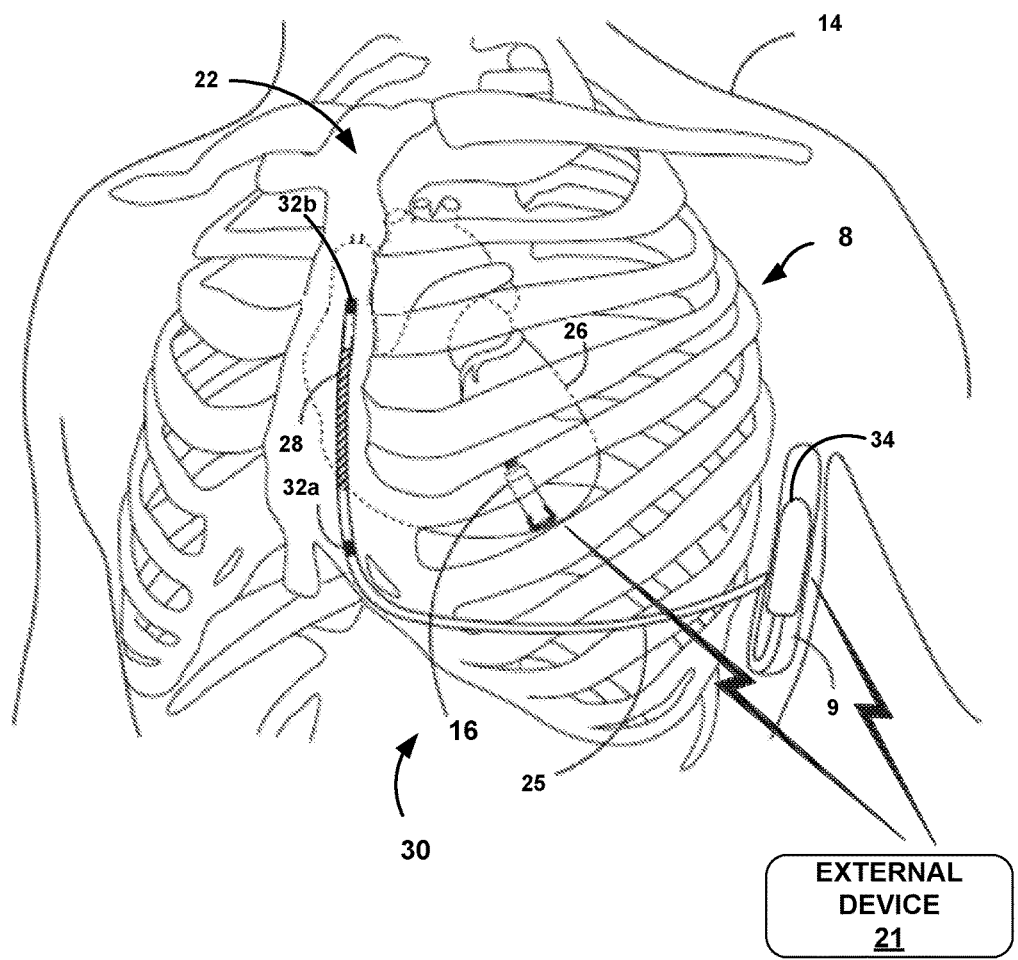
FIG. 1 is an example front view of a patient implanted with an example medical device system that includes an extracardiovascular ICD system and a intracardiac pacing device (IPD) implanted within a cardiac chamber of the patient in accordance with one or more aspects of the present disclosure.

FIG. 1 is a front view of an example medical device system 8 that includes an extracardiovascular ICD system 30 and IPD 16 implanted within a patient. In the example of FIG. 1, extracardiovascular ICD system 30 includes ICD 9 coupled to a cardiac defibrillation lead 25, which extends subcutaneously above the ribcage from ICD 9. In the illustrated example, defibrillation lead 25 extends toward a center of the torso of patient 14, bends or turns near the center of the torso, and extends subcutaneously superior above the ribcage and/or sternum 22. Defibrillation lead 25 may be offset laterally to the left or the right of sternum 22 or located over sternum 22. Defibrillation lead 25 may extend substantially parallel to sternum 22 or be angled lateral from the sternum at either the proximal or distal end.

Defibrillation lead 25 includes an insulative lead body having a proximal end that includes a connector 34 configured to be connected to ICD 9 and a distal portion that includes one or more electrodes. Defibrillation lead 25 also includes one or more conductors that form an electrically conductive path within the lead body and interconnect the electrical connector and respective ones of the electrodes. In the example of FIG. 1, defibrillation lead 25 includes a single defibrillation electrode 28 toward the distal portion of defibrillation lead 25, e.g., toward the portion of defibrillation lead 25 extending along sternum 22. Defibrillation lead 25 is placed along sternum such that a therapy vector between defibrillation electrode 28 and a housing electrode formed by or on ICD 9 (or other second electrode of the therapy vector) is substantially across a ventricle of heart 26.

Defibrillation lead 25 may also include one or more sensing electrodes, such as sensing electrodes 32a and 32b, located along the distal portion of defibrillation lead 25. In the example illustrated in FIG. 1, sensing electrodes 32a and 32b are separated from one another by defibrillation electrode 28. In other examples, however, sensing electrodes 32a and 32b may be both distal of defibrillation electrode 28 or both proximal of defibrillation electrode 28. In other examples, lead 25 may include more or fewer electrodes at various locations proximal and/or distal to defibrillation electrode 28, and lead 25 may include multiple defibrillation electrodes, e.g., defibrillation electrodes 28a and 28b. IPD 16 may be configured to detect shocks delivered by ICD 9 via lead 25.

Figure 2A:
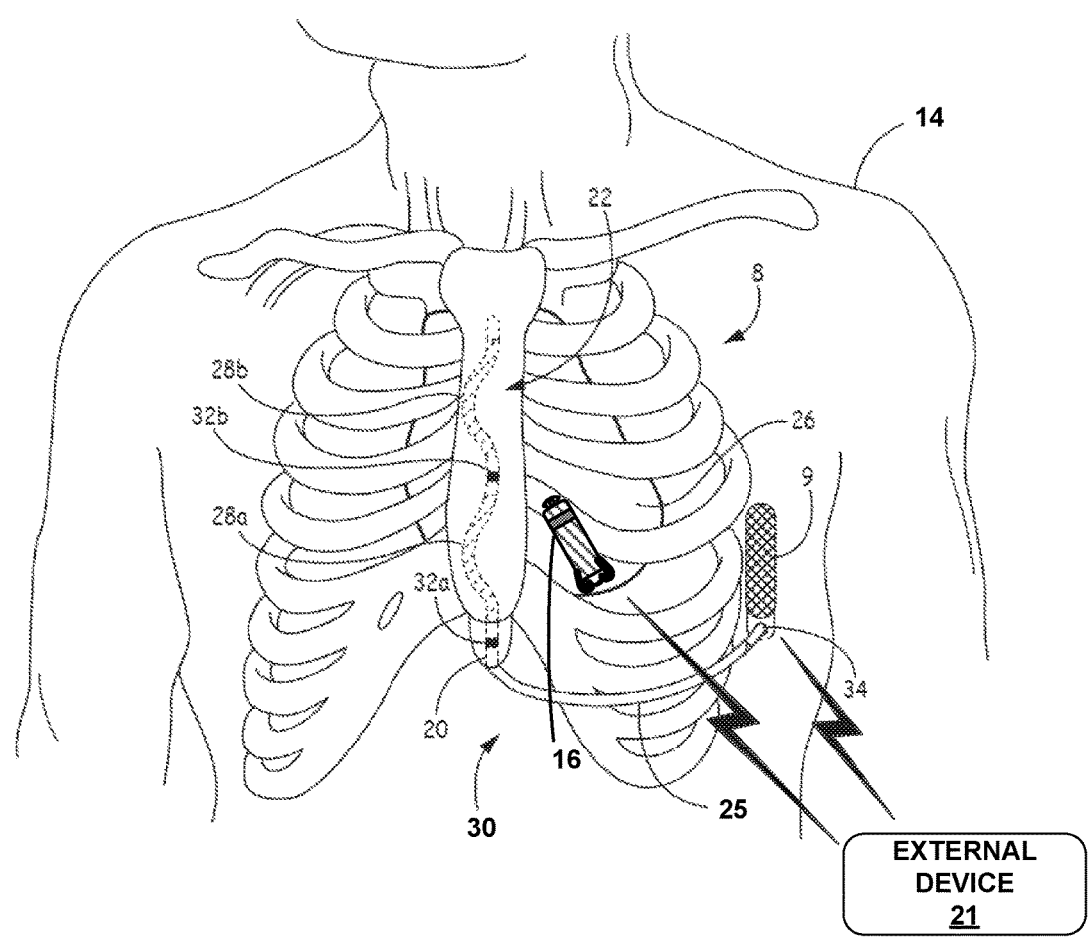
FIG. 2A is an example front view of a patient implanted with another example medical device system that includes an extracardiovascular ICD system and a intracardiac pacing device (IPD) implanted within a cardiac chamber of the patient in accordance with one or more aspects of the present disclosure.
Figure 2B:
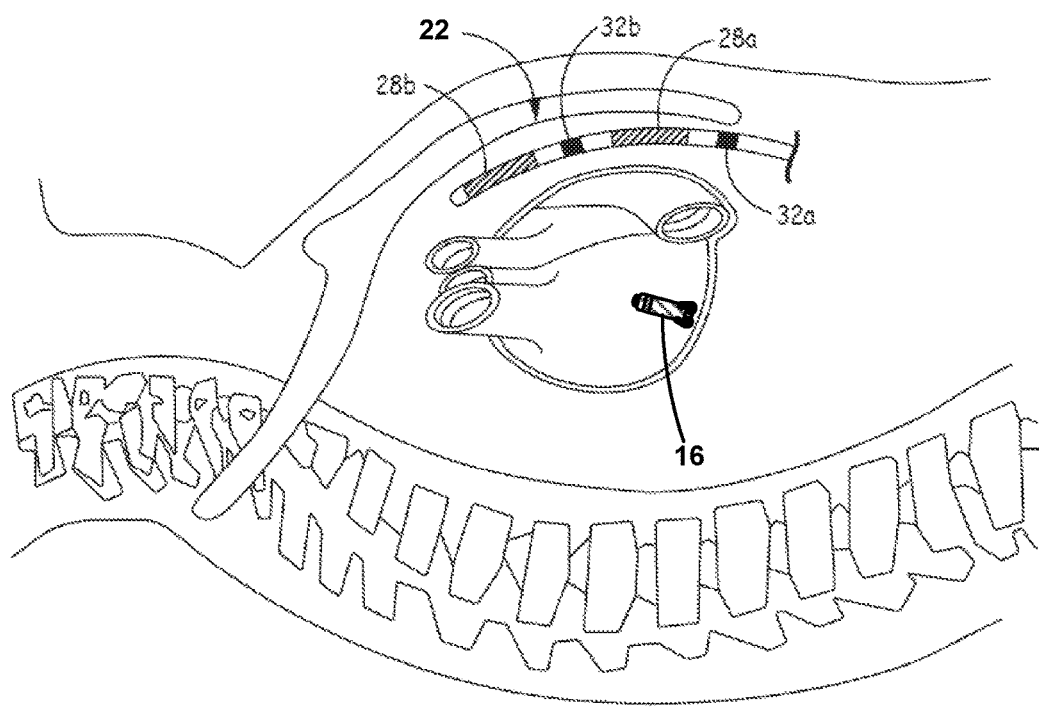
FIG. 2B is an example side view of a patient implanted with the example medical device system of FIG. 2A in accordance with one or more aspects of the present disclosure.
Figure 2C:
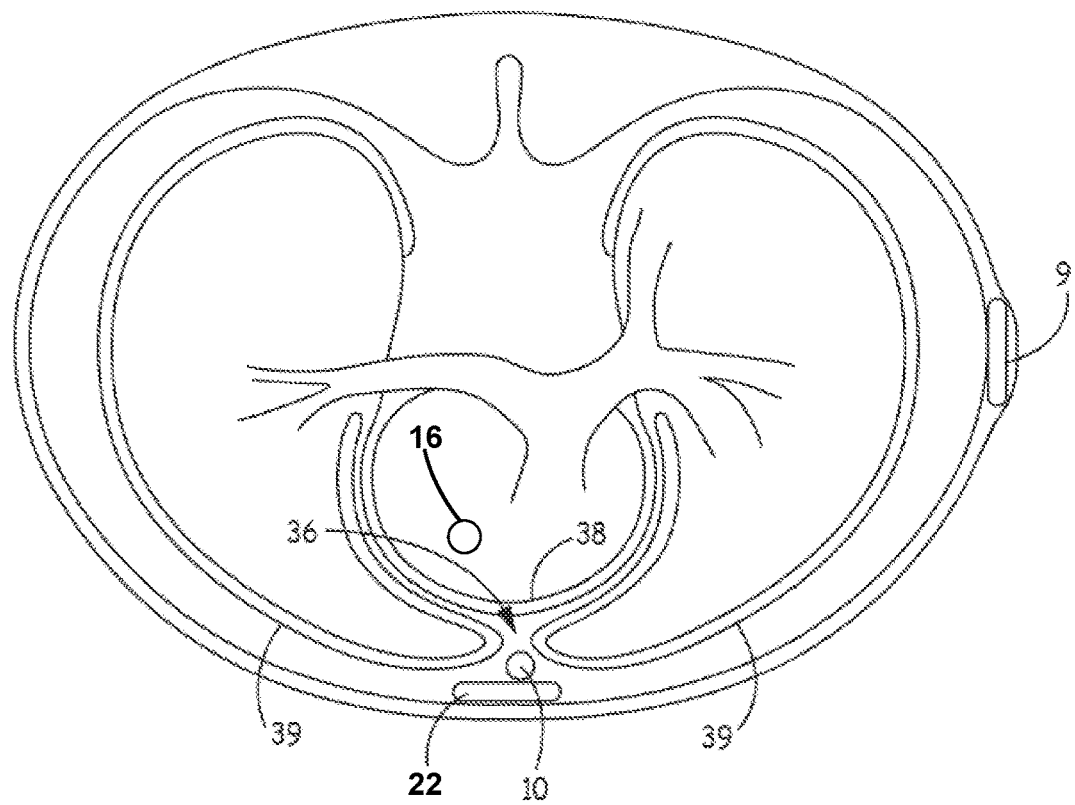
FIG. 2C is an example transverse view of a patient implanted with the example medical device system of FIG. 2A in accordance with one or more aspects of the present disclosure.

FIG. 2A, FIG. 2B, and FIG. 2C are conceptual diagrams illustrating various views of another example cardiac medical device system 8 implanted within a patient 14. Components with like numbers in FIG. 1, FIG. 2A, FIG. 2B, and FIG. 2C may be similarly configured and may provide similar functionality. With reference to FIG. 2A, cardiac system 8 includes an extracardiovascular ICD system 30 implanted in patient 14 and an intracardiac pacing device (IPD) 16 implanted within heart 26 of patient 14. FIG. 2A is a front view of a patient implanted with the cardiac system 8 of FIG. 2A. FIG. 2B is a side view of the patient implanted with the cardiac system 8 of FIG. 2A. FIG. 2C is a transverse view of the patient implanted with the cardiac system 8 of FIG. 2A. Medical device system 8 as illustrated in FIG. 2A, FIG. 2B, and FIG. 2C may be configured to perform one or more of the techniques described herein with respect to medical device system 8 of FIG. 1.

Referring again to FIG. 2A, ICD system 30 includes an implantable cardiac defibrillator (ICD) 9 connected to at least one implantable cardiac defibrillation lead 25. ICD 9 is configured to deliver high-energy cardioversion or defibrillation pulses to a patient's heart when atrial or ventricular fibrillation is detected. Cardioversion shocks are typically delivered in synchrony with a detected R-wave when fibrillation detection criteria are met. Defibrillation pulses are typically delivered when fibrillation criteria are met, and the R-wave cannot be discerned from signals sensed by ICD 9.

ICD 9 of FIG. 2A is implanted subcutaneously or submuscularly on the left side of patient 14 above the ribcage. Unlike defibrillation lead 25 of FIG. 1, defibrillation lead 25 of FIG. 2A may be implanted at least partially in a substernal location in FIG. 2A, e.g., between the ribcage and/or sternum 22 and heart. In one such configuration, a proximal portion of lead 25 extends subcutaneously from ICD 9 toward the sternum and a distal portion of lead 25 extends superior under or below the sternum 22 in the anterior mediastinum 36. The anterior mediastinum 36 is bounded laterally by the pleurae 39 (see FIG. 2C), posteriorly by the pericardium, and anteriorly by the sternum 22. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 25 extends along the posterior side of the sternum 22 substantially within the loose connective tissue and/or substernal musculature of the anterior mediastinum. Lead 25 may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum 22 or ribcage.

In other examples, lead 25 may be implanted at other extracardiovascular locations. For example, defibrillation lead 25 may extend subcutaneously above the ribcage from ICD 9 toward a center of the torso of patient 14, bend or turn near the center of the torso, and extend subcutaneously superior above the ribcage and/or sternum 22, similar to that shown in FIG. 1. Defibrillation lead 25 may be offset laterally to the left or the right of the sternum 22 or located over the sternum 22. Defibrillation lead 25 may extend substantially parallel to the sternum 22 or be angled lateral from the sternum 22 at either the proximal or distal end.

Defibrillation lead 25 of FIG. 2A includes an insulative lead body having a proximal end that includes a connector configured to be connected to ICD 9 and a distal portion that includes one or more electrodes. Defibrillation lead 25 also includes one or more conductors that form an electrically conductive path within the lead body and interconnect the electrical connector and respective ones of the electrodes.

Defibrillation lead 25 of FIG. 2A includes a defibrillation electrode that includes two sections or segments 28*a* and 28*b*, collectively (or alternatively) defibrillation electrodes 28. The defibrillation electrodes 28 of FIG. 2A are toward the distal portion of defibrillation lead 25, e.g., toward the portion of defibrillation lead 25 extending along the sternum 22. Defibrillation lead 25 of FIG. 2A is placed below and/or along sternum 22 such that a therapy vector between defibrillation electrodes 28*a* or 28*b* and a housing electrode formed by or on ICD 9 (or other second electrode of the therapy vector) is substantially across a ventricle of heart 26. The therapy vector may, in one example, be viewed as a line that extends from a point on defibrillation electrodes 28 (e.g., a center of one of the defibrillation electrode sections 28*a* or 28*b*) to a point on the housing electrode of ICD 9. Defibrillation electrode 28 of FIG. 2A may, in one example, be an elongated coil electrode.

Defibrillation lead 25 may also include one or more sensing electrodes, such as sensing electrodes 32*a* and 32*b*, located along the distal portion of defibrillation lead 25. In the example illustrated in FIG. 2A and FIG. 2B, sensing electrodes 32*a* and 32*b* are separated from one another by defibrillation electrode 28*a*. In other examples, however, sensing electrodes 32*a* and 32*b* may be both distal of defibrillation electrode 28 or both proximal of defibrillation electrode 28. In other examples, lead 25 may include more or fewer electrodes at various locations proximal and/or distal to defibrillation electrode 28. In the same or different examples, ICD 9 may include one or more electrodes on another lead (not shown).

ICD system 30 may sense electrical signals via one or more sensing vectors that include combinations of electrodes 32*a* and 32*b* and the housing electrode of ICD 9. For example, ICD 9 may obtain electrical signals sensed using a sensing vector between electrodes 32*a* and 32*b*, obtain electrical signals sensed using a sensing vector between electrode 32*b* and the conductive housing electrode of ICD 9, obtain electrical signals sensed using a sensing vector between electrode 32*a* and the conductive housing electrode of ICD 9, or a combination thereof. In some instances, ICD 9 may sense cardiac electrical signals using a sensing vector that includes one of the defibrillation electrode sections 28*a* and 28*b* (or electrode 28 in FIG. 1) and one of sensing electrodes 32*a* and 32*b* or the housing electrode of ICD 9.

The sensed electrical intrinsic signals may include electrical signals generated by cardiac muscle and indicative of depolarizations and repolarizations of heart 26 at various times during the cardiac cycle. Additionally, the sensed electrical signals may also include electrical signals, e.g., pacing pulses, generated and delivered to heart 26 by IPD 16. ICD 9 analyzes the electrical signals sensed by the one or more sensing vectors to detect tachyarrhythmia, such as ventricular tachycardia or ventricular fibrillation. In response to detecting the tachyarrhythmia, ICD 9 may begin to charge a storage element, such as a bank of one or more capacitors, and, when charged, deliver one or more defibrillation pulses via defibrillation electrodes 28 (e.g., 28, 28*a*, 28*b*) of defibrillation lead 25 if the tachyarrhythmia is still present.

In the example of FIG. 2A, IPD 16 is implanted within the right ventricle of heart 26 to sense electrical activity of heart 26 and deliver pacing therapy, e.g., anti-tachycardia pacing (ATP) therapy, bradycardia pacing therapy, and/or post-shock pacing, to heart 26. IPD 16 may be attached to an interior wall of the right ventricle of heart 26 via one or more fixation elements that penetrate the tissue. These fixation elements may secure IPD 16 to the cardiac tissue and retain an electrode (e.g., a cathode or an anode) in contact with the cardiac tissue. However, in other examples, system 8 may include additional pacing devices 16 within respective chambers of heart 26 (e.g., right or left atrium and/or left ventricle). In further examples, IPD 16 may be attached to an external surface of heart 26 (e.g., in contact with the epicardium) such that IPD 16 is disposed outside of heart 26.

IPD 16 may be capable sensing electrical signals using the electrodes carried on the housing of IPD 16. These electrical signals may be electrical signals generated by cardiac muscle and indicative of depolarizations and repolarizations of heart 26 at various times during the cardiac cycle. IPD 16 may analyze the sensed electrical signals to detect tachyarrhythmias, such as ventricular tachycardia or ventricular fibrillation. In response to detecting the tachyarrhythmia, IPD 16 may, e.g., depending on the type of tachyarrhythmia, begin to deliver ATP therapy via the electrodes of IPD 16. In addition to or instead of ATP therapy, IPD 16 may also deliver bradycardia pacing therapy and post-shock pacing.

Cardiac IPD 16 and ICD system 30 may be configured to operate completely independent of one another. In such a case, IPD 16 and ICD system 30 are not capable of establishing telemetry or other communication sessions with one another to exchange information about sensing and/or therapy using one-way or two-way communication. Instead, each of IPD 16 and ICD system 30 analyze the data sensed via their respective electrodes to make tachyarrhythmia detection and/or therapy decisions. As such, each device does not know if the other will detect the tachyarrhythmia, if or when it will provide therapy, and the like.

During a tachyarrhythmia that could be treated with either ATP or an anti-tachyarrhythmia shock, e.g., cardioversion or defibrillation shock, it is important to ensure that anti-tachyarrhythmia therapies do not overlap or that ATP therapy does not take place after the defibrillation pulse. Applying ATP after a defibrillation pulse could be pro-arrhythmic and present a hazard to the patient. Moreover, it would be desirable for IPD 16 to deliver post-shock pacing after delivery of a cardioversion/defibrillation pulse. Systems could be designed to provide device-to-device communication between ICD system 30 and IPD 16, but this may add complexity to the system and not be highly effective or fast enough to prevent unwanted ATP therapies post defibrillation pulse or too slow to initiate post-shock pacing therapies. In some examples described herein, IPD 16 may be configured to detect anti-tachyarrhythmia shocks delivered by ICD 9, which improve the coordination of therapy between subcutaneous ICD 9 and IPD 16 without requiring device-to-device communication. Although ICD 9 and IPD 16 may not require or utilize device-to-device communication to coordinate tachyarrhythmia therapy, the devices may still communicate with one another for other reasons, as described below in further detail.

Although FIG. 2A is shown or described in the context of a substernal ICD system 30 and a IPD 16, techniques in accordance with one or more aspects of the present disclosure may be applicable to other coexistent systems. For example, an ICD system may include a lead having a distal portion that is implanted subcutaneously above the sternum (or other location) instead of being implanted substernally, in a manner similar to that shown in FIG. 1. As another example, instead of an intracardiac pacing device, a pacing system may be implanted having a pacemaker and one or more leads connected to and extending from the pacemaker into one or more chambers of the heart or attached to the outside of the heart to provide pacing therapy to the one or more chambers. As such, the examples of FIG. 1, FIG. 2A, FIG. 2B, and FIG. 2C are illustrated for example purposes only and should not be considered limiting of the techniques described herein.

External device 21 may be configured to communicate with one or both of ICD system 30 and IPD 16. In examples where external device 21 only communicates with one of ICD system 30 and IPD 16, the non-communicative device may receive instructions from or transmit data to the device in communication with device 21. In some examples, device 21 comprises a handheld computing device, computer workstation, or networked computing device. Device 21 may include a user interface that receives input from a user. In other examples, the user may also interact with device 21 remotely via a networked computing device. The user may interact with device 21 to communicate with IPD 16 and/or ICD system 30. For example, the user may interact with device 21 to send an interrogation request and retrieve therapy delivery data, update therapy parameters that define therapy, manage communication between IPD 16 and/or ICD system 30, or perform any other activities with respect to IPD 16 and/or ICD system 30. Although the user is a physician, technician, surgeon, electrophysiologist, or other healthcare professional, the user may be patient 14 in some examples.

Device 21 may also allow the user to define how IPD 16 and/or ICD system 30 senses electrical signals (e.g., ECGs), detects arrhythmias (e.g., tachyarrhythmias), delivers therapy, and communicates with other devices of system 8. For example, device 21 may be used to change tachyarrhythmia detection parameters. In another example, device 21 may be used to manage therapy parameters that define therapies such as anti-tachyarrhythmia shocks and/or ATP.

In examples in which IPD 16 and ICD system 30 communicate, device 21 may be used to alter communication protocols between IPD 16 and ICD system 30. For example, device 21 may instruct IPD 16 and/or ICD system 30 to switch between one-way and two-way communication and/or change which of IPD 16 and/or ICD system 30 are tasked with initial detection of arrhythmias.

Device 21 may communicate with IPD 16 and/or ICD system 30 via wireless communication using any techniques known in the art. Examples of communication techniques may include, for example, proprietary and non-proprietary radiofrequency (RF) telemetry, inductive telemetry, acoustics, and TCC, but other techniques are also contemplated. During TCC (tissue conduction communication), current is driven through the tissue between two or more electrodes of a transmitting device. The electrical signal spreads and can be detected at a distance by measuring the voltage generated between two electrodes of a receiving device. In some examples, device 21 may include a programming head that may be placed proximate to the patient's body near the IPD 16 and/or ICD system 30 implant site in order to improve the quality or security of communication between IPD 16 and/or ICD system 30 and device 21.

IPD 16 may be configured to adjust cardiac therapy based on the application of anti-tachyarrhythmia shock therapy by ICD 9. It may be useful that IPD 16 knows when ICD 9 has delivered tachyarrhythmia shock therapy. In response to the delivery of the shock, IPD 16 may terminate ATP and activate post-shock pacing.

In some examples, IPD 16 and ICD system 30 may engage in communication to facilitate the appropriate detection of arrhythmias and/or delivery of anti-tachycardia therapy. Anti-tachycardia therapy may include anti-tachyarrhythmia shocks (e.g., cardioversion or defibrillation pulses) and/or anti-tachycardia pacing (ATP). The communication may include one-way communication in which one device is configured to transmit communication messages and the other device is configured to receive those messages. The communication may instead include two-way communication in which each device is configured to transmit and receive communication messages. Although the examples below describe detection of tachyarrhythmias and the delivery of anti-tachyarrhythmia shocks and/or ATP, IPD 16 and ICD system 30 may be configured to communicate with each other and provide alternative electrical stimulation therapies. Two-way communication and coordination of the delivery of patient therapies between IPD 16 and ICD system 30 is described in commonly-assigned U.S. patent application Ser. No. 13/756,085, titled, "SYSTEMS AND METHODS FOR LEADLESS PACING AND SHOCK THERAPY," filed Jan. 31, 2013, the entire content of which is incorporated by reference herein.

In combination with, or as an alternative to, communication between IPD 16 and ICD system 30, IPD 16 may be configured to detect an anti-tachyarrhythmia shock delivered by ICD system 30 or an external defibrillator according to the detection of an electrical signal across two or more electrodes of IPD 16. IPD 16 may be configured to detect an anti-tachyarrhythmia shock based on electrical characteristics of the anti-tachyarrhythmia shock. Even though different defibrillation devices may provide different waveforms, including different pulse durations and amplitudes, defibrillation pulses generally have electrical signal characteristics such that detection of an anti-tachyarrhythmia shock can occur even without prior knowledge as to an anti-tachyarrhythmia shock waveform of an implanted or external defibrillator. In this manner, IPD 16 may coordinate the delivery of cardiac stimulation therapy, including the termination of ATP and the initiation of the delivery of post-shock pacing, with the application of an anti-tachyarrhythmia shock merely through the detection of defibrillation pulses and without the need to communicate with the defibrillation device applying the anti-tachyarrhythmia shock.

In some examples, IPD 16 detects the anti-tachyarrhythmia shock by measuring the voltage across the electrode inputs of the implanted device. IPD 16 may detect one or more signal characteristics of an anti-tachyarrhythmia shock including: detection of the high amplitude level of an anti-tachyarrhythmia shock, detection of a high slew rate of the leading and trailing edges, and detection of a large post-shock polarization change. Detection of more than one signal characteristic may improve sensitivity and/or specificity. For example, IPD 16 may detect a high level of an anti-tachyarrhythmia shock in combination with one or both of the detection of a high slew rate of the leading and trailing edges, and the detection of a large post-shock polarization change.

In one example, IPD 16 may be configured to receive an indication of a detected cardiac arrhythmia eligible for anti-tachyarrhythmia shock therapy. IPD 16 may include a set of electrodes configured to be implanted within or near heart 26 of patient 14. In response to receiving the indication of the tachyarrhythmia, IPD 16 may enable shock detection circuitry of IPD 16 configured to detect delivery of anti-tachyarrhythmia shock therapy. The shock detection circuitry may then detect delivery of anti-tachyarrhythmia shock therapy by measuring the voltage across the electrode inputs (e.g., detect that the shock has been delivered). The shock detection circuitry may apply one or more of three general techniques for detection of an anti-tachyarrhythmia shock: detection of the high level of an anti-tachyarrhythmia shock, detection of a high slew rate of the leading and trailing edges, and detection of a large post-shock polarization change. Each technique looks for a different electrical signal characteristic. The three techniques may be combined to improve sensitivity and/or specificity. For example, the high level of an anti-tachyarrhythmia shock may be combined with one or both of the detection of a high slew rate of the leading and trailing edges, and the detection of a large post-shock polarization change.

In response to detection of the anti-tachyarrhythmia shock, the IPD 16 may abort and/or temporarily suspend the delivery of ATP and to activate post-shock pacing, such as VVI (Ventricular sensing, Ventricular pacing, Inhibited pacing when activity sensed) post-shock pacing. ATP may remain suspended temporarily following an anti-tachyarrhythmia shock to insure that the relatively higher-rate pacing pulses will not induce another arrhythmia. Additionally, post-shock pacing may be used to insure pacing support if the patient's heart does not begin to beat normally immediately following an anti-tachyarrhythmia shock. The pacing device may deliver post-shock pacing with a higher than normal pulse amplitude and pulse width (relative to typical cardiac pacing) to minimize the risk of loss of capture following an anti-tachyarrhythmia shock. A higher capture threshold may occur as a result of tissue stunning due to elevated current in the myocardial tissue from the anti-tachyarrhythmia shock delivery. A higher threshold may also occur as a result of physiological changes in the tissue resulting from lack of blood flow to the myocardium during ventricular fibrillation (VF). Furthermore, after an anti-tachyarrhythmia shock there can be increased polarization at the lead interface resulting in the need for a higher voltage to overcome the lead polarization.

In one example, IPD 16 may deliver post-shock pacing to heart 26 via at least a subset of the set of electrodes of IPD 16. In some examples, IPD 16 may deliver the post-shock pacing after entering a post-shock pacing mode in response to detecting the shock. In some examples, IPD 16 may use a timer to determine when a predetermined time has elapsed, during which the shock should have been delivered. IPD 16 may begin post-shock pacing after the predetermined period has elapsed and/or stop post-shock pacing.

IPD 16 may receive the indication of the detected cardiac tachyarrhythmia in a variety of ways. For example, IPD 16 may sense, via at least a subset of the set of electrodes, an electrical signal from heart 26. IPD 16 may then detect, from the electrical signal, a cardiac tachyarrhythmia eligible for anti-tachyarrhythmia shock therapy. In this manner, IPD 16 may receive the indication of the detected arrhythmia via direct detection of the arrhythmia at IPD 16. In another example, ICD system 30 may be configured to transmit a communication including the indication to IPD 16. The indication of the detected arrhythmia may thus be received from ICD system 30, for example. IPD 16 may receive a communication from ICD system 30 indicating that a cardiac arrhythmia was detected by ICD system 30. Alternatively, IPD 16 may receive a communication from ICD system 30 indicating that a shock is impending.

Detection of the anti-tachyarrhythmia shock may be used to abort and/or temporarily suspend the delivery of ATP and to activate post-shock pacing, such as VVI post-shock pacing. ATP may be temporarily suspended following an anti-tachyarrhythmia shock to insure that the pacing pulses will not induce another arrhythmia. For example, ATP may be temporarily suspended following an anti-tachyarrhythmia shock until the current arrhythmia has been terminated or until a short period of time has elapsed to prevent interfering with the subcutaneous ICD.

In addition to the delivery of ATP, IPD 16 may be configured to deliver post-shock pacing to heart 26. After delivery of an anti-tachyarrhythmia shock, heart 26 may benefit from pacing to return to a normal sinus rhythm (e.g., if heart 26 has developed bradycardia or asystole) or otherwise recover from receiving the shock. In some examples, IPD 16 and/or ICD system 30 may be configured to detect bradycardia or asystole. In some examples, this post-shock pacing may be automatically delivered in response to the IPD 16 detecting that a shock was delivered. Post-shock pacing may be used to ensure pacing support if the patient's heart does not begin to beat normally immediately following an anti-tachyarrhythmia shock. A higher than normal amplitude and pulse width is commonly used to minimize the risk of loss of capture following an anti-tachyarrhythmia shock. A higher capture threshold may occur as a result of tissue stunning due to elevated current in the myocardial tissue from the anti-tachyarrhythmia shock delivery. A higher threshold may also occur as a result of physiological changes in the tissue resulting from lack of blood flow to the myocardium during VF. Furthermore, after an anti-tachyarrhythmia shock there can be increased polarization at the lead interface resulting in the need for a higher voltage to overcome the lead polarization.

In some examples, IPD 16 may enable the shock detection circuitry when ATP is delivered to heart 26, in anticipation of a shock. In some examples, IPD 16 may enable the shock detection circuitry in response to detecting a fast rate, such as a tachyarrhythmia (e.g., when communication between IPD 16 and ICD system 30 is not present or is unreliable). The tachyarrhythmia may be detected based on sensed electrical signals and/or mechanical signals from heart 26. In some examples, the shock detection circuitry may be disabled until an indication of an arrhythmia is terminated or impending shock is received.

IPD 16 may also be configured to disable the shock detection circuitry. For example, IPD 16 may be configured to track a period of time following detection of delivery of anti-tachyarrhythmia shock therapy. The period of time may be a predetermined period of time and/or tracked with a timer, for example. IPD 16 may also determine that the period of time exceeds a timeout threshold, and, in response to the determination, disable the shock detection circuitry. IPD 16 may disable the shock detection circuitry when not needed to conserve battery power, for example.

IPD 16 may also re-start post-shock pacing if additional shocks are detected. For example, IPD 16 may be configured to detect a first shock and begin delivery of the post-shock pacing if needed (e.g., bradycardia or systole has been detected). IPD 16 may subsequently detect the delivery of a second shock, and, in response to the detection of the second shock, re-start delivery of the post-shock pacing if needed. IPD 16 may continue to re-start post-shock pacing as long as additional shocks are delivered. However, IPD 16 may be configured to stop re-starting post-shock pacing after a predetermined number of shocks, or in response to ICD system 30 transmitting a message instructing IPD 16 to stop delivery of post-shock pacing. IPD 16 and/or ICD system 30 may implement an intrinsic beat detector or other algorithm to distinguish between intrinsic beats and potential artifacts caused by pacing and/or shock therapy. IPD 16 may also deliver ATP upon detection of a tachyarrhythmia, and terminate ATP if a defibrillation pulse is detected. IPD 16 may initiate post-shock pacing and/or, upon detection of additional tachyarrhythmia following the shock, resume ATP.

In some examples, IPD 16 may terminate post-shock pacing in response to various indicators. For example, IPD 16 may track a period of time following the start of post-shock pacing. IPD 16 may then determine that the period of time exceeds a timeout threshold. For example, IPD 16 may use a timer to track this period of time. In response to the determination, IPD 16 may terminate delivery of post-shock pacing. In other examples, IPD 16 may terminate post-shock pacing after delivery of a predetermined number of pacing pulses. Alternatively, IPD 16 may terminate post-shock pacing in response to detection of a normal sinus rhythm or receiving a communication from ICD system 30 instructing IPD 16 to terminate post-shock pacing.

Although IPD 16 is generally described as delivering post-shock pacing, in other examples, different implanted devices may provide post-shock pacing. For example, IPD 16 may be configured to deliver ATP, but a different IPD implanted in a different chamber of heart 26 may be configured to detect a shock and deliver the post-shock pacing to heart 26. In other examples, the implanted device delivering post-shock pacing may not be an intracardiac pacing device or leadless pacing device. For example, an implantable pacing device, separate from an ICD delivering the anti-tachyarrhythmia shock, may include one or more leads for delivering post-shock pacing therapy to one or more locations of heart 26. As another example, an ICD delivering the anti-tachyarrhythmia shock may deliver post-shock pacing, whereas IPD is configured to provide ATP, and not post-shock pacing.

Some ICD systems, such as ICD system 30 in FIG. 1, may have limited capabilities to deliver anti-tachycardia pacing and post-shock pacing as well as conventional brady pacing therapy. In some examples, another device, such as IPD 16, may be used to deliver such pacing therapies. In particular, delivery of anti-tachycardia pacing (ATP) therapy by a device such as IPD 16 may be helpful in treating tachycardia episodes. However, when using ATP therapy to treat a tachycardia episode, there may be risks associated with delivering ATP therapy. For example, although the risk may be small, it is possible that delivery of ATP therapy will not successfully terminate certain tachycardia episodes, and may in some cases result in an acceleration of the tachycardia, potentially worsening the tachycardia episode, and presenting a hazard to the patient.

In cases where ATP therapy is not successful in terminating a tachycardia episode, or where ATP therapy results in an undesirable acceleration of the tachycardia, additional treatment may be warranted or required. In such cases, one possible additional treatment involves the delivery of an anti-tachyarrhythmia shock, or a high voltage shock (HV shock), to terminate the tachycardia episode.

Some devices, such as IPD 16, do not also have the capability to deliver a HV shock. So if ATP therapy be unsuccessful in treating the tachycardia episode, another device, such as ICD system 30, may be relied upon to deliver further treatment, which may include an HV shock. In such a system, ICD system 30 may serve as a backup device that may provide functionality not provided by a pacing device such as IPD 16.

However, in systems where ICD system 30 might not be present, or where ICD system 30 cannot be relied upon to deliver an HV shock, it may be beneficial for IPD 16 to operate differently. For example, if IPD 16 is implanted in a patient where no other device is available to deliver an HV shock, delivery of ATP therapy may not be appropriate, and may even be counterproductive. Accordingly, in a system where no device can be relied upon to deliver an HV shock, it may be appropriate for IPD 16 to refrain from initiating delivery of ATP therapy. Disabling delivery of ATP therapy, which may prevent delivery of ATP therapy to treat a tachycardia episode, may in some cases be preferable to delivering ATP therapy to treat a tachycardia episode.

Figure 3:
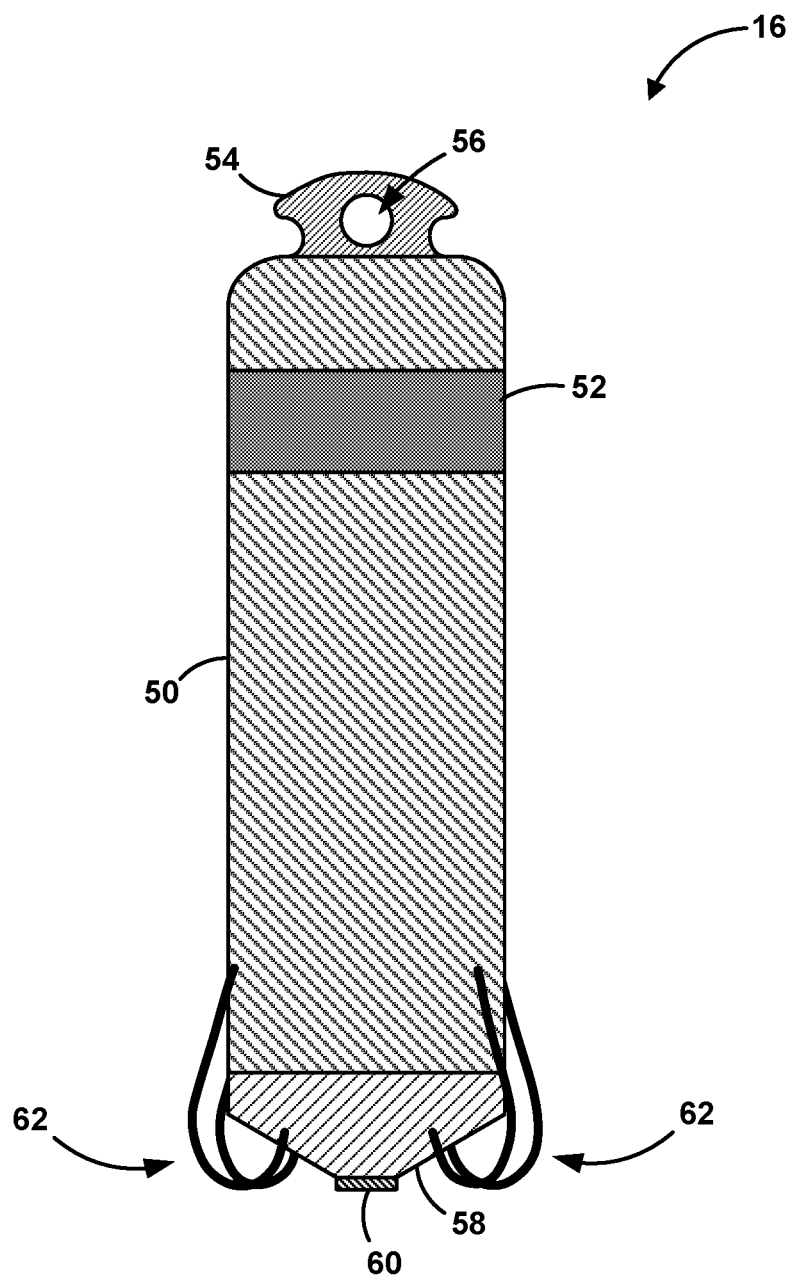
FIG. 3 is a conceptual drawing illustrating the example IPD of FIG. 1 in accordance with one or more aspects of the present disclosure.

FIG. 3 is a conceptual drawing illustrating example IPD 16 of FIG. 1 that may include shock detection circuitry and/or utilize the shock detection techniques of this disclosure. As shown in FIG. 3, IPD 16 includes case 50, cap 58, electrode 60, electrode 52, fixation mechanisms 62, flange 54, and opening 56. Together, case 50 and cap 58 may be considered the housing of IPD 16. In this manner, case 50 and cap 58 may enclose and protect the various electrical components within IPD 16. Case 50 may enclose substantially all of the electrical components, and cap 58 may seal case 50 and create the hermetically sealed housing of IPD 16. Although IPD 16 is generally described as including one or more electrodes, IPD 16 may typically include at least two electrodes (e.g., electrodes 52 and 60) to deliver an electrical signal (e.g., therapy such as ATP) and/or provide at least one sensing vector.

Electrodes 52 and 60 are carried on the housing created by case 50 and cap 58. In this manner, electrodes 52 and 60 may be considered leadless electrodes. In the example of FIG. 3, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating. Electrode 60 may be used as a cathode and electrode 52 may be used as an anode, or vice versa, for delivering pacing stimulation therapy such as ATP or post-shock pacing. However, electrodes 52 and 60 may be used in any stimulation configuration. In addition, electrodes 52 and 60 may be used to detect intrinsic electrical signals from cardiac muscle. In other examples, IPD 16 may include three or more electrodes, where each electrode may deliver therapy and/or detect intrinsic signals. ATP delivered by IPD 16, as compared with alternative devices, may be considered to be "painless" to patient 14 or even undetectable by patient 14 since the electrical stimulation occurs very close to or at cardiac muscle and at relatively low energy levels.

Fixation mechanisms 62 may attach IPD 16 to cardiac tissue. Fixation mechanisms 62 may be active fixation tines, screws, clamps, adhesive members, or any other types of attaching a device to tissue. As shown in the example of FIG. 3, fixation mechanisms 62 may be constructed of a memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of IPD 16. For example, a suture or other device may be inserted around flange 54 and/or through opening 56 and attached to tissue. In this manner, flange 54 may provide a secondary attachment structure to tether or retain IPD 16 within heart 26 if fixation mechanisms 62 fail. Flange 54 and/or opening 56 may also be used to extract IPD 16 once the IPD needs to be explanted (or removed) from patient 14 if such action is deemed necessary.

The techniques described herein are generally described with regard to a leadless pacing device or intracardiac pacing device such as IPD 16. IPD 16 may be an example of an anti-tachycardia pacing device (ATPD). However, alternative implantable medical devices may be used to perform the same or similar functions as IPD 16 (e.g., delivering ATP to heart 26) and communicate with ICD system 30. For example, an ATPD may include a small housing that carries an electrode, similar to IPD 16, and configured to be implanted within a chamber of heart 26. The ATPD may also include one or more relatively short leads configured to place one or more respective additional electrodes at another location within the same chamber of the heart or a different chamber of the heart. This configuration may be referred to as an Intercardiac Pacing Device. In this manner, the housing of the ATPD may not carry all of the electrodes used to deliver ATP or perform other functions. In other examples, each electrode of the ATPD may be carried by one or more leads (e.g., the housing of the ATPD may not carry any of the electrodes).

In another example, the ATPD may be configured to be implanted external to heart 26, e.g., near or attached to the epicardium of heart 26. An electrode carried by the housing of the ATPD may be placed in contact with the epicardium and/or one or more electrodes of leads coupled to the ATPD may be placed in contact with the epicardium at locations sufficient to provide therapy such as ATP (e.g., on external surfaces of the left and/or right ventricles). In some example, ICD system 30 may communicate with one or more leadless or leaded devices implanted internal or external to heart 26.

Figure 4:
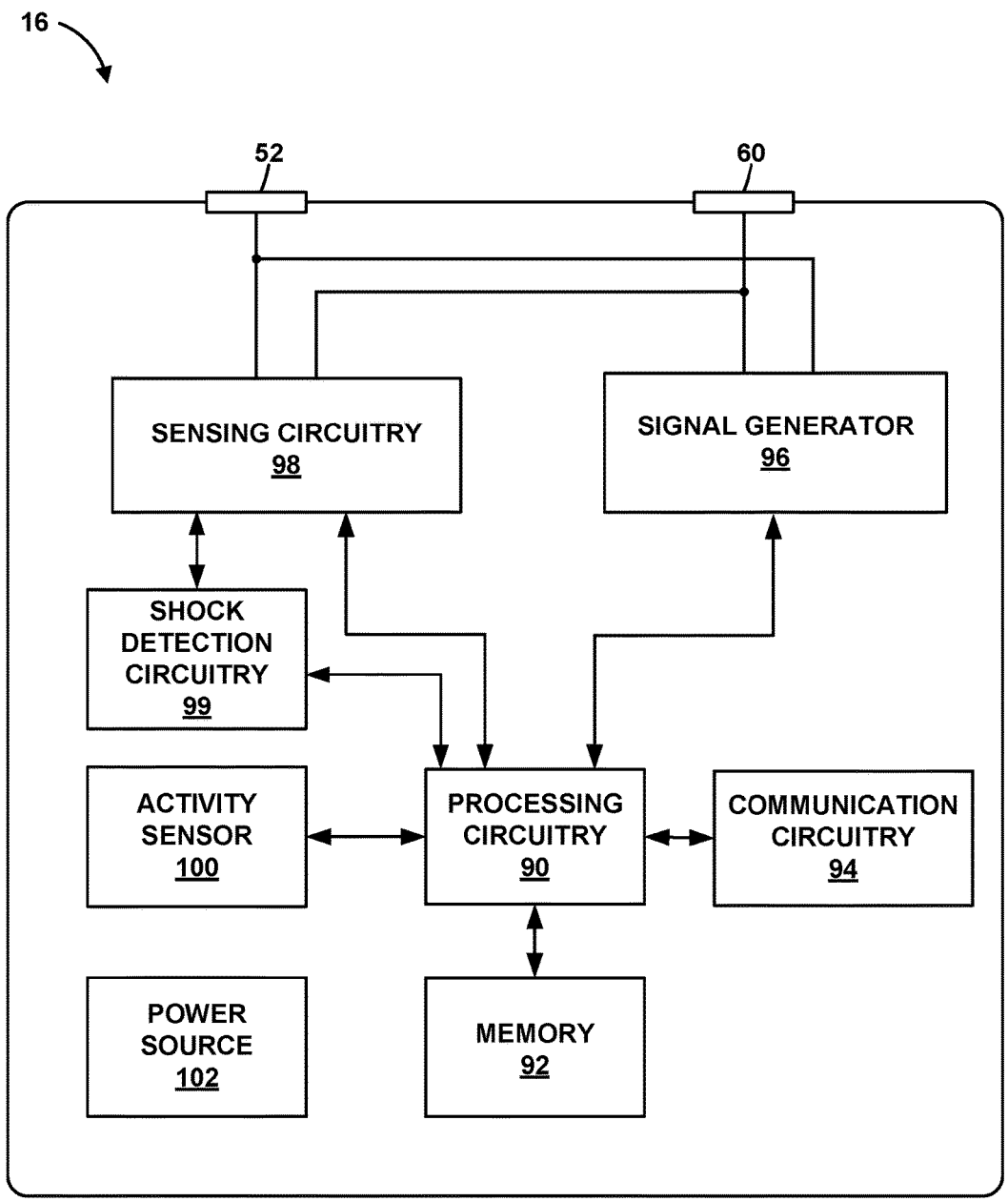
FIG. 4 is a functional block diagram illustrating an example configuration of the IPD of FIG. 1 in accordance with one or more aspects of the present disclosure.

FIG. 4 is a functional block diagram illustrating an example configuration of IPD 16 of FIG. 1. In the illustrated example, IPD 16 includes a processing circuitry 90, memory 92, signal generation circuitry 96, sensing circuitry 98, shock detection circuitry 99, activity sensor 100, communication circuitry 94, and power source 102. Memory 92 includes computer-readable instructions that, when executed by processing circuitry 90, cause IPD 16 and processing circuitry 90 to perform various functions attributed to IPD 16 and processing circuitry 90 herein (e.g., detecting arrhythmias, communicating with ICD system 30, and delivering anti-tachycardia pacing and post-shock pacing as well as conventional brady pacing therapy). Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 90 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 90 may include multiple components, such as any combination of one or more microprocessors, one or more controllers, one or more DSPs, one or more ASICs, or one or more FPGAs, as well as other discrete or integrated logic circuitry. The functions attributed to processing circuitry 90 herein may be embodied as software, firmware, hardware or any combination thereof.

Processing circuitry 90 controls signal generation circuitry 96 to deliver stimulation therapy to heart 26 according to therapy parameters, which may be stored in memory 92. For example, processing circuitry 90 may control signal generation circuitry 96 to deliver electrical pulses with the amplitudes, pulse widths, frequency, or electrode polarities specified by the therapy parameters. In this manner, signal generation circuitry 96 may deliver pacing pulses (e.g., ATP pulses or post-shock pacing therapy, or conventional bradycardia pacing pulses) to heart 26 via electrodes 52 and 60. Although IPD 16 may only include two electrodes, e.g., electrodes 52 and 60, IPD 16 may utilize three or more electrodes in other examples. IPD 16 may use any combination of electrodes to deliver therapy and/or detect electrical signals from patient 14.

Signal generation circuitry 96 is electrically coupled to electrodes 52 and 60 carried on the housing of IPD 16. In the illustrated example, signal generation circuitry 96 is configured to generate and deliver electrical stimulation therapy to heart 26. For example, signal generation circuitry 96 may deliver the electrical stimulation therapy to a portion of cardiac muscle within heart 26 via electrodes 52 and 60. In some examples, signal generation circuitry 96 may deliver pacing stimulation, e.g., ATP therapy or post-shock pacing, in the form of voltage or current electrical pulses. In other examples, signal generation circuitry 96 may deliver one or more of these types of stimulation in the form of other signals, such as sine waves, square waves, or other substantially continuous time signals. Although IPD 16 is generally described as delivering pacing pulses, IPD 16 may deliver cardioversion or defibrillation pulses in other examples.

ATP may be delivered to patient 14 as defined by a set of parameters, which may be stored in memory 92. These parameters may include pulse intervals, pulse width, current and/or voltage amplitudes, and durations for each pacing mode. For example, the pulse interval may be based on a fraction of the detected ventricular tachycardia (VT) cycle length and be between approximately 150 milliseconds and 500 milliseconds (e.g., between approximately 2.0 hertz and 7.0 hertz), and the pulse width may be between approximately 0.5 milliseconds and 2.0 milliseconds. The amplitude of each pacing pulse may be between approximately 2.0 volts and 10.0 volts. In some examples, the pulse amplitude may be approximately 6.0 V and the pulse width may be approximately 1.5 milliseconds; another example may include pulse amplitudes of approximately 5.0 V and pulse widths of approximately 1.0 milliseconds. Each train of pulses during ATP may last for a duration of between approximately 0.5 seconds to approximately 15 seconds or be defined as a specific number of pulses. Each pulse, or burst of pulses, may include a ramp up in amplitude or in pulse rate. In addition, trains of pulses in successive ATP periods may be delivered at increasing pulse rate in an attempt to capture the heart and terminate the tachycardia. Example ATP parameters and other criteria involving the delivery of ATP are described in U.S. Pat. No. 6,892,094 to Ousdigian et al., entitled, "COMBINED ANTI-TACHYCARDIA PACING (ATP) AND HIGH VOLTAGE THERAPY FOR TREATING VENTRICULAR ARRHYTHMIAS," and issued on May 10, 2005, the entire content of which is incorporated herein by reference.

Parameters that define post-shock pacing may also vary. In one example, monophasic post-shock pacing therapy may have a pulse width of approximately 1 millisecond at each phase and a pulse amplitude of approximately 5 volts. The pacing rate may be set to 30-60 beats per minute (0.5-1 hertz). The duration of each post-shock pacing session may be between 10 seconds and 60 seconds, or even longer in other examples. In other examples, pulse widths, pulse amplitudes, and/or durations of post-shock pacing may be greater or lower.

Electrical sensing circuitry 98 monitors signals from electrodes 52 and 60 in order to monitor electrical activity of heart 26, impedance, or other electrical phenomenon. Sensing may be done to determine heart rates or heart rate variability, or to detect arrhythmias (e.g., tachyarrhythmias or bradycardia) or other electrical signals. Sensing circuitry 98 may also include a switch module to select which of the available electrodes (or electrode polarity) are used to sense the heart activity, depending upon which electrode combination, or electrode vector, is used in the current sensing configuration. In examples with several electrodes, processing circuitry 90 may select the electrodes that function as sense electrodes, i.e., select the sensing configuration, via the switch module within sensing circuitry 98. Sensing circuitry 98 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processing circuitry 90, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processing circuitry 90 may control the functionality of sensing circuitry 98 by providing signals via a data/address bus.

Processing circuitry 90 may include a timing and control module, which may be embodied as hardware, firmware, software, or any combination thereof. The timing and control module may comprise a dedicated hardware circuit, such as an ASIC, separate from other processing circuitry 90 components, such as a microprocessor, or a software module executed by a component of processing circuitry 90, which may be a microprocessor or ASIC. The timing and control module may implement programmable counters. If IPD 16 is configured to generate and deliver pacing pulses to heart 26, such counters may control the basic time intervals associated with DDD, VVI, DVI, VDD, AAI, DDI, DDDR, VVIR, DVIR, VDDR, AAIR, DDIR and other modes of pacing. Example IPDs that may deliver pacing using such modes are described in U.S. patent application Ser. No. 13/665,492 to Bonner et al., entitled, "LEADLESS PACEMAKER SYSTEM," and filed on Oct. 31, 2012, or in U.S. patent application Ser. No. 13/665,601 to Bonner et al., entitled, "LEADLESS PACEMAKER SYSTEM," and filed on Oct. 31, 2012. U.S. patent application Ser. No. 13/665,492 to Bonner et al. and U.S. patent Ser. No. 13/665,601 to Bonner et al. are both incorporated herein by reference in their entireties.

Intervals defined by the timing and control module within processing circuitry 90 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing circuitry 98 for a time interval during and after delivery of electrical stimulation to heart 26. The durations of these intervals may be determined by processing circuitry 90 in response to stored data in memory 92. The timing and control module of processing circuitry 90 may also determine the amplitude of the cardiac pacing pulses.

Interval counters implemented by the timing and control module of processing circuitry 90 may be reset upon sensing of R-waves and P-waves with detection channels of sensing circuitry 98. In examples in which IPD 16 provides pacing, signal generation circuitry 96 may include pacer output circuits that are coupled to electrodes 52 and 60, for example, appropriate for delivery of a bipolar or unipolar pacing pulse to one of the chambers of heart 26. In such examples, processing circuitry 90 may reset the interval counters upon the generation of pacing pulses by signal generation circuitry 96, and thereby control the basic timing of cardiac pacing functions, including ATP or post-shock pacing.

The value of the count present in the interval counters when reset by sensed R-waves and P-waves may be used by processing circuitry 90 to measure the durations of R-R intervals, P-P intervals, P-R intervals and R-P intervals, which are measurements that may be stored in memory 92. Processing circuitry 90 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 92 may be configured as a plurality of recirculating buffers, capable of holding series of measured intervals, which may be analyzed by processing circuitry 90 in response to the occurrence of a pace or sense interrupt to determine whether the patient's heart 26 is presently exhibiting atrial or ventricular tachyarrhythmia.

In some examples, an arrhythmia detection method may include any suitable tachyarrhythmia detection algorithms. In one example, processing circuitry 90 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processing circuitry 90 in other examples.

In some examples, processing circuitry 90 may determine that tachyarrhythmia has occurred by identification of shortened R-R (or P-P) interval lengths. Generally, processing circuitry 90 detects tachycardia when the interval length falls below 220 milliseconds and fibrillation when the interval length falls below 180 milliseconds. In other examples, processing circuitry 70 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 92. This interval length may need to be detected for a certain number of consecutive cycles, for a certain percentage of cycles within a running window, or a running average for a certain number of cardiac cycles, as examples. In other examples, additional physiological parameters may be used to detect an arrhythmia. For example, processing circuitry 90 may analyze one or more morphology measurements, impedances, or any other physiological measurements to determine that patient 14 is experiencing a tachyarrhythmia.

In the event that an ATP regimen is desired, timing intervals for controlling the generation of ATP therapies by signal generation circuitry 96 may be loaded by processing circuitry 90 into the timing and control module to control the operation of the escape interval counters therein and to define refractory periods during which detection of R-waves and P-waves is ineffective to restart the escape interval counters for the ATP. An ATP regimen may be desired if processing circuitry 90 detects an atrial or ventricular tachyarrhythmia based on signals from sensing circuitry 98, and/or receives a command from another device or system, such as ICD system 30, as examples.

In addition to detecting and identifying specific types of cardiac rhythms, sensing circuitry 98 may also sample the detected intrinsic signals to generate an electrogram or other time-based indication of cardiac events. Processing circuitry 90 may also be able to coordinate the delivery of pacing pulses from different IPDs implanted in different chambers of heart 26, such as an IPD implanted in atrium and/or an IPD implanted in left ventricle. For example, processing circuitry 90 may identify delivered pulses from other IPDs via sensing circuitry 98 and update pulse timing to accomplish a selected pacing regimen. This detection may be on a pulse-to-pulse or beat-to-beat basis, or on a less frequent basis to make slight modifications to pulse rate over time. In other examples, IPDs may communicate with each other via communication circuitry 94 and/or instructions over a carrier wave (such as a stimulation waveform). In this manner, ATP or post-shock pacing may be coordinated from multiple IPDs.

Shock detection circuitry 99 may be used to detect anti-tachyarrhythmia shocks delivered by ICD system 30 or another device. For example, processing circuitry 90 may enable shock detection circuitry 99 in response to detecting a tachyarrhythmia or receiving a communication indicating that an arrhythmia has been detected or a shock is imminent. Processing circuitry 90 may also disable shock detection circuitry 99 after a predetermined time period has elapsed or when a shock is otherwise not (or no longer) anticipated. When shock detection circuitry 99 is enabled, shock detection circuitry 99 may identify when an electrical signal received by sensing circuitry 98 is representative of a cardioversion or defibrillation pulse.

In response to detecting a shock via shock detection circuitry 99, processing circuitry 90 may begin post-shock pacing when such functionality has been enabled for therapy. Processing circuitry 90 may also re-start post-shock pacing in response to detecting additional shocks via shock detection circuitry 99. In some examples, processing circuitry 90 may terminate ATP upon detection of a shock.

Shock detection circuitry 99 may detect an anti-tachyarrhythmia shock, e.g., a defibrillation or cardioversion pulse, delivered by ICD system 30 or an external defibrillator based on the detection of an electrical signal across two or more electrodes. In order to detect the anti-tachyarrhythmia shock, shock detection circuitry 99 may detect one or more signal characteristics of an anti-tachyarrhythmia shock including: detection of the high amplitude level of an anti-tachyarrhythmia shock, detection of a high slew rate of the leading and trailing edges, and detection of a large post-shock polarization change. Detection of more than one signal characteristic may improve sensitivity and/or specificity of the shock anti-tachyarrhythmia shock detection. For example, shock detection circuitry 99 may detect a high level of an anti-tachyarrhythmia shock in combination with one or both of the detection of a high slew rate of the leading and trailing edges and/or the detection of a large post-shock polarization change. Example shock detection circuitry is described in U.S. Pat. No. 9,278,229 to Reinke et al., entitled "Anti-tachyarrhythmia shock detection," which issued on Mar. 8, 2016, is hereby incorporated by reference.

Although illustrated separately in the example of FIG. 4, shock detection circuitry 99 may, in some examples, be included as part of processing circuitry 90. In some examples, the shock detection functionality attributed to shock detection circuitry 99 may be a functional module executed by processing circuitry 90.

Memory 92 may be configured to store a variety of operational parameters, therapy parameters, sensed and detected data, and any other information related to the therapy and treatment of patient 14. In the example of FIG. 4, memory 92 may store sensed ECGs, detected arrhythmias, communications from ICD system 30, and therapy parameters that define ATP and/or post-shock pacing regimens. In other examples, memory 92 may act as a temporary buffer for storing data until it can be uploaded to ICD system 30, another implanted device, or device 21.

Activity sensor 100 may be contained within the housing of IPD 16 and include one or more accelerometers or other devices capable of detecting motion and/or position of IPD 16. For example, activity sensor 100 may include a 3-axis accelerometer that is configured to detect accelerations in any direction in space. Specifically, the 3-axis accelerator may be used to detect IPD 16 motion that may be indicative of cardiac events and/or noise. For example, processing circuitry 90 may monitor the accelerations from activity sensor 100 to confirm or detect arrhythmias. Since IPD 16 may move with a chamber wall of heart 26, the detected changes in acceleration may also be indicative of contractions. Therefore, IPD 16 may be configured to identify heart rates and confirm arrhythmias, such as a tachycardia, sensed via sensing circuitry 98.

Communication circuitry 94 includes any suitable hardware, firmware, software or any combination thereof for communicating with another device, such as device 21 or ICD system 30 (FIG. 1). Under the control of processing circuitry 90, communication circuitry 94 may receive downlink telemetry from and send uplink telemetry to device 21 with the aid of an antenna, which may be internal and/or external. Processing circuitry 90 may provide the data to be uplinked to device 21 and the control signals for the telemetry circuit within communication circuitry 94, e.g., via an address/data bus. In some examples, communication circuitry 94 may provide received data to processing circuitry 90 via a multiplexer.

In some examples, IPD 16 may signal device 21 to further communicate with and pass the alert through a network such as the Medtronic CareLink® Network developed by Medtronic, Inc., of Minneapolis, Minn., or some other network linking patient 14 to a clinician. IPD 16 may spontaneously transmit information to the network or in response to an interrogation request from a user.

Power source 102 may be any type of device that is configured to hold a charge to operate the circuitry of IPD 16. Power source 102 may be provided as a rechargeable or non-rechargeable battery. In other examples, power source 102 may incorporate an energy scavenging system that stores electrical energy from movement of IPD 16 within patient 14.

Processing circuitry 90 may detect an enable event as a result of initialization of IPD 16 or as a result of a power-on cycle. In other examples, processing circuitry 90 may detect an enable event based on input from sensing circuitry 98, signal generation circuitry 96, shock detection circuitry 99, or activity sensor 100. In other examples, an enable event may be detected based on logic within processing circuitry 90 or based on processing circuitry 90 executing instructions stored in memory 92. In still further examples, communication circuitry 94 within IPD 16 may detect input or a signal from another device operated by a clinician, and may output an indication of an enable event to processing circuitry 90, which may determine, based on the indication of the enable event, that an enable event has been received.

Processing circuitry 90 may operate to control signal generation circuitry 96 when enabling or disabling ATP therapy. Processing circuitry 90 within IPD 16 may enable delivery of anti-tachyarrhythmia pacing (ATP) therapy (504) by outputting to signal generation circuitry 96 information that causes signal generation circuitry 96 to enable delivery of ATP, or in other examples, processing circuitry 90 may control signal generation circuitry 96 in a way that results in enabling delivery of ATP. Disabling delivery of ATP may include processing circuitry 90 outputting to signal generation circuitry 96 information that causes signal generation circuitry 96 to disable delivery of ATP, or in other examples, may include processing circuitry 90 controlling signal generation circuitry 96 in such a way that results in disabling delivery of ATP.

Figure 5:
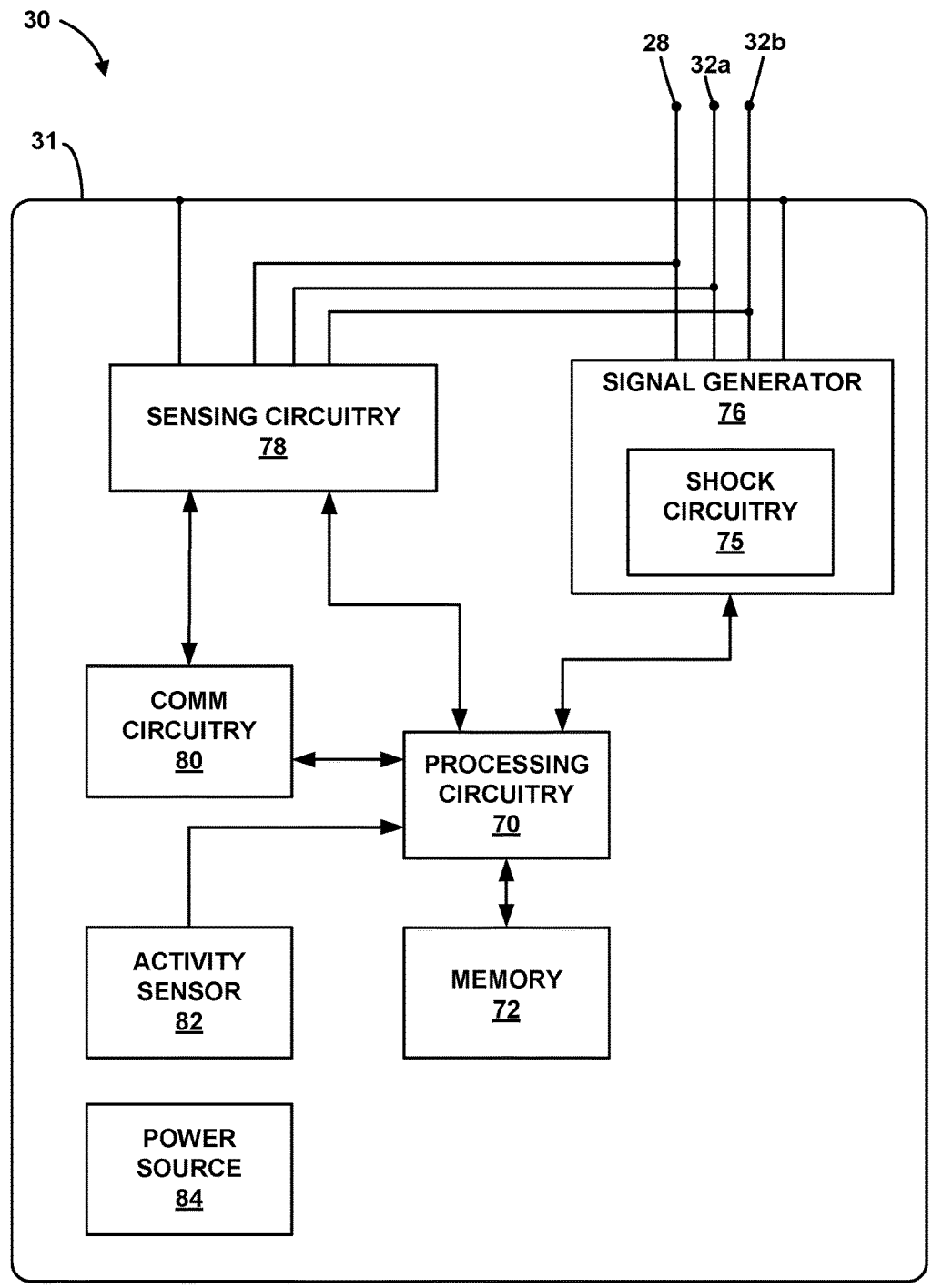
FIG. 5 is a functional block diagram illustrating an example configuration of the ICD of FIG. 1 in accordance with one or more aspects of the present disclosure.

FIG. 5 is a functional block diagram illustrating an example configuration of ICD system 30 of FIG. 1. As described in connection with FIG. 1, ICD system 30 includes ICD 9 connected to at least one implantable cardiac defibrillation lead 25. As shown in FIG. 5, ICD system 30 includes a processing circuitry 70, memory 72, shock circuitry 75, signal generation circuitry 76, sensing circuitry 78, communication circuitry 80, activity sensor 82, and power source 84. Memory 72 includes computer-readable instructions that, when executed by processing circuitry 70, cause ICD system 30 and processing circuitry 70 to perform various functions attributed to ICD system 30 and processing circuitry 70 herein (e.g., detection of tachyarrhythmias, communication with IPD 16, and/or delivery of anti-tachyarrhythmia shock therapy). Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 70 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 70 may include multiple components, such as any combination of one or more microprocessors, one or more controllers, one or more DSPs, one or more ASICs, or one or more FPGAs, as well as other discrete or integrated logic circuitry. The functions attributed to processing circuitry 70 herein may be embodied as software, firmware, hardware or any combination thereof.

Processing circuitry 70 controls signal generation circuitry 76 to deliver stimulation therapy to heart 26 according to therapy parameters, which may be stored in memory 72. For example, processing circuitry 70 may control signal generation circuitry 76 to deliver electrical pulses (e.g., shock pulses) with the amplitudes, pulse widths, frequency, or electrode polarities specified by the therapy parameters. In this manner, signal generation circuitry 76 may deliver electrical pulses to heart 26 via electrodes 28 (or 28a or 28b) and the conductive housing electrode 31 of ICD 9. In addition, via any combination of electrodes, 28, 32a, 32b and/or housing 31 may be connected to sensing circuitry 78. In further examples, signal generation circuitry 76 may deliver electrical pulses to heart 26 via any combination of electrodes, 28, 32a, 32b and/or housing 31, although electrodes 32a and 32b, may more frequently be used for sensing. ICD system 30 may use any combination of electrodes to deliver anti-tachycardia therapy and/or detect electrical signals from patient 14. However, in general, coil electrode 28 and housing 31 may be used to deliver an anti-tachyarrhythmia shock.

Signal generation circuitry 76 may also include shock circuitry 75. Shock circuitry 75 may include circuitry and/or capacitors required to deliver an anti-tachyarrhythmia shock. For example, signal generation circuitry 76 may charge shock circuitry 75 to prepare for delivering a shock. Shock circuitry 75 may then discharge to enable signal generation circuitry 76 to deliver the shock to patient 14 via one or more electrodes. In other examples, shock circuitry 75 may be located within ICD system 30 but outside of signal generation circuitry 76.

Signal generation circuitry 76 is electrically coupled to electrodes 28, 32a, and 32b. In the illustrated example, signal generation circuitry 76 is configured to generate and deliver electrical anti-tachyarrhythmia shock therapy to heart 26. For example, signal generation circuitry 76 may, using shock circuitry 75, deliver shocks to heart 26 via a subset of electrodes 28, 32a, and 32b. In some examples, signal generation circuitry 76 may deliver pacing stimulation (e.g., post-shock pacing), and cardioversion or defibrillation pulses in the form of voltage or current electrical pulses. In other examples, signal generation circuitry 76 may deliver one or more of these types of stimulation or shocks in voltage or current in the form of other signals, such as sine waves, square waves, or other substantially continuous time signals.

Signal generation circuitry 76 may include a switch module and processing circuitry 70 may use the switch module to select, e.g., via a data/address bus, which of the available electrodes are used to deliver shock and/or pacing pulses. The switch module may include a switch array, switch matrix, multiplexer, or any other type of switching device suitable to selectively couple stimulation energy to selected electrodes.

Electrical sensing circuitry 78 may be configured to monitor signals from at least two of the electrodes 28, 32a, 32b and housing 31 in order to monitor electrical activity of heart 26, impedance, or other electrical phenomenon. Sensing may be done to determine heart rates or heart rate variability, or to detect arrhythmias (e.g., tachyarrhythmia) or other electrical signals. Sensing circuitry 78 may also include a switch module to select which of the available electrodes are used to sense the heart activity, depending upon which electrode combination, or electrode vector, is used in the current sensing configuration. In examples with several electrodes, processing circuitry 70 may select the electrodes that function as sense electrodes, i.e., select the sensing configuration, via the switch module within sensing module 78. Sensing module 78 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processing circuitry 70, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processing circuitry 70 may control the functionality of sensing module 78 by providing signals via a data/address bus.

Processing circuitry 70 may include a timing and control module, which may be embodied as hardware, firmware, software, or any combination thereof. The timing and control module may comprise a dedicated hardware circuit, such as an ASIC, separate from other processing circuitry 70 components, such as a microprocessor, or a software module executed by a component of processing circuitry 70, which may be a microprocessor or ASIC. The timing and control module may implement programmable counters. If ICD system 30 is configured to generate and deliver pacing pulses to heart 26, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processing circuitry 70 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing circuitry 78 for a time interval during and after delivery of electrical stimulation to heart 26. The durations of these intervals may be determined by processing circuitry 70 in response to stored data in memory 72. The timing and control module of processing circuitry 70 may also determine the amplitude of the cardiac pacing pulses.

Interval counters implemented by the timing and control module of processing circuitry 70 may be reset upon sensing of R-waves and P-waves with detection channels of sensing circuitry 78. The value of the count present in the interval counters when reset by sensed R-waves and P-waves may be used by processing circuitry 70 to measure the durations of R-R intervals, P-P intervals, P-R intervals and R-P intervals, which are measurements that may be stored in memory 72. Processing circuitry 70 may use the count in the interval counters to detect a tachyarrhythmia event, such as AF, AT, VF, or VT. These intervals may also be used to detect the overall heart rate, ventricular contraction rate, and heart rate variability. A portion of memory 72 may be configured as a plurality of recirculating buffers, capable of holding series of measured intervals, which may be analyzed by processing circuitry 70 in response to the occurrence of a pace or sense interrupt to determine whether the patient's heart 26 is presently exhibiting atrial or ventricular tachyarrhythmia.

In some examples, an arrhythmia detection method may include any suitable tachyarrhythmia detection algorithms. In one example, processing circuitry 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processing circuitry 70 in other examples.

In some examples, processing circuitry 70 may determine that tachyarrhythmia has occurred by identification of shortened R-R (or P-P) interval lengths. Generally, processing circuitry 70 detects tachycardia when the interval length falls below 220 milliseconds and fibrillation when the interval length falls below 180 milliseconds. In other examples, processing circuitry 70 may detect ventricular tachycardia when the interval length falls between 330 milliseconds and ventricular fibrillation when the interval length falls between 240 milliseconds. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In the event that processing circuitry 70 detects an atrial or ventricular tachyarrhythmia based on signals from sensing circuitry 78, and an anti-tachyarrhythmia pacing regimen is desired, timing intervals for controlling the generation of anti-tachyarrhythmia pacing therapies by signal generation circuitry 76 may be loaded by processing circuitry 70 into the timing and control module to control the operation of the escape interval counters therein and to define refractory periods during which detection of R-waves and P-waves is ineffective to restart the escape interval counters for the an anti-tachyarrhythmia pacing. In addition to detecting and identifying specific types of cardiac rhythms, sensing circuitry 78 may also sample the detected intrinsic signals to generate an electrogram or other time-based indication of cardiac events.

In some examples, communication circuitry 80 may be used to detect communication signals from IPD 16. Instead, IPD 16 may generate electrical signals via one or more electrodes with amplitudes and/or patterns representative of information to be sent to ICD system 30. The electrical signals may be carried by pacing pulses or separate communication signals configured to be detected by ICD system 30. In this manner, communication circuitry 80 may be configured to monitor signals sensed by sensing circuitry 78 and determine when a communication message is received from IPD 16.

In other examples, ICD system 30 may also transmit communication messages to IPD 16 using electrical signals transmitted from one or more of electrodes 28, 32a, 32b and housing 31. In this case, communication circuitry 80 may be coupled to signal generation circuitry 76 to control the parameters of generated electrical signals or pulses. Alternatively, processing circuitry 70 may detect communications via sensing circuitry 78 and/or generate communications for deliver via signal generation circuitry 76. Although communication circuitry 80 may be used to communicate using electrical signals via electrodes 28, 32a, 32b and housing 31, communication circuitry 80 may alternatively or in addition use wireless protocols, such as RF telemetry, inductive telemetry, acoustics, or TCC to communicate with IPD 16 or other medical devices. In some examples, communication circuitry 80 may include this wireless communication functionality.

Communication circuitry 80 includes any suitable hardware, firmware, software or any combination thereof for communicating with another device, such as device 21 (FIG. 1). Communication circuitry 80 may transmit generated or received arrhythmia data, therapy parameter values, communications between ICD system 30 and IPD 16, or any other information. For example, communication circuitry 80 may transmit information representative of sensed physiological data such as R-R intervals or any other data that may be used by IPD 16 to determine a condition of patient 14. Communication circuitry 80 may also be used to receive updated therapy parameters from device 21. Under the control of processing circuitry 70, communication circuitry 80 may receive downlink telemetry from and send uplink telemetry to device 21 with the aid of an antenna, which may be internal and/or external. Processing circuitry 70 may provide the data to be uplinked to device 21 and the control signals for the telemetry circuit within communication circuitry 80, e.g., via an address/data bus. In some examples, communication circuitry 80 may provide received data to processing circuitry 70 via a multiplexer.

Memory 72 may be configured to store a variety of operational parameters, therapy parameters, sensed and detected data, and any other information related to the monitoring, therapy and treatment of patient 14. Memory 72 may store, for example, thresholds and parameters indicative of tachyarrhythmias and/or therapy parameter values that at least partially define delivered anti-tachyarrhythmia shocks. In some examples, memory 72 may also store communications transmitted to and/or received from IPD 16.

Activity sensor 82 may be contained within the housing of ICD system 30 and include one or more accelerometers or other devices capable of detecting motion and/or position of ICD system 30. For example, activity sensor 82 may include a 3-axis accelerometer that is configured to detect accelerations in any direction in space. Accelerations detected by activity sensor 82 may be used by processing circuitry 70 to identify potential noise in signals detected by sensing circuitry 78 and/or confirm the detection of arrhythmias or other patient conditions.

In some examples, ICD system 30 may signal device 21 to further communicate with and pass the alert through a network such as the Medtronic CareLink® Network developed by Medtronic, Inc., of Minneapolis, Minn., or some other network linking patient 14 to a clinician. ICD system 30 may spontaneously transmit the diagnostic information to the network or in response to an interrogation request from a user.

Power source 84 may be any type of device that is configured to hold a charge to operate the circuitry of ICD system 30. Power source 84 may be provided as a rechargeable or non-rechargeable battery. In other examples, power source 84 may also incorporate an energy scavenging system that stores electrical energy from movement of ICD system 30 within patient 14.

Some ICD systems, such as ICD system 30 in FIG. 5, may have limited capabilities to deliver anti-tachycardia pacing and post-shock pacing as well as conventional brady pacing therapy. In some examples, another device, such as IPD 16 (shown in FIG. 4), may be used to deliver such pacing therapies. In particular, delivery of anti-tachycardia pacing (ATP) therapy by a device such as IPD 16 may be helpful in treating tachycardia episodes. However, when using ATP therapy to treat a tachycardia episode, there is a risk that the delivery of ATP therapy will not successfully terminate certain tachycardia episodes. Further, delivery of ATP therapy may in some cases result in an acceleration of the tachycardia, potentially worsening the tachycardia episode, and presenting a hazard to the patient.

In cases where ATP therapy is not successful in terminating a tachycardia episode, or where ATP therapy results in an undesirable acceleration of the tachycardia, additional treatment may be warranted or required. In such cases, one possible additional treatment involves the delivery of an anti-tachyarrhythmia shock, or a high voltage shock (HV shock), to terminate the tachycardia episode. Accordingly, in some examples, treatment of a tachycardia episode may initially include delivery of ATP therapy. And in some cases where ATP therapy is not successful in terminating a tachycardia episode, treatment may include additional therapy, such as the delivery of an HV shock.

Some devices that are configured to deliver ATP therapy, such as IPD 16, do not also have the capability to deliver a HV shock. In an example where IPD 16 may not have the ability to deliver an HV shock, IPD 16 may nevertheless deliver ATP therapy to treat tachycardia episodes. Should ATP therapy be unsuccessful in treating the tachycardia episode, another device, such as ICD system 30 (shown in FIG. 5), may be relied upon to deliver further treatment, which may include an HV shock. In such a system, ICD system 30 may serve as a backup device that may provide functionality not provided by a pacing device such as IPD 16.

However, in systems where ICD system 30 might not be present, or where ICD system 30 cannot be relied upon to deliver an HV shock, it may be appropriate for IPD 16 to operate differently. For example, if IPD 16 is implanted in a patient where there is no ICD system 30 and no other device is available to deliver an HV shock, delivery of ATP therapy may not be appropriate, and may even be counterproductive, since in some cases, delivery of ATP therapy may lead to an acceleration of the tachycardia. Further, in situations where both IPD 16 and another device, such as ICD system 30, are implanted in a patient as shown in FIG. 1, it is possible that ICD system 30 cannot be relied upon to deliver an HV shock. Such situations may include instances where ICD system 30 may not be operating properly, may be nearing the end of its useful life, or may have limited remaining battery power. Accordingly, in a system where no device can be relied upon to deliver an HV shock, it may be appropriate for IPD 16 to refrain from initiating delivery of ATP therapy. Disabling delivery of ATP therapy, which may prevent delivery of ATP therapy to treat a tachycardia episode, may in some cases be preferable to delivering ATP therapy to treat a tachycardia episode.

Figure 6:
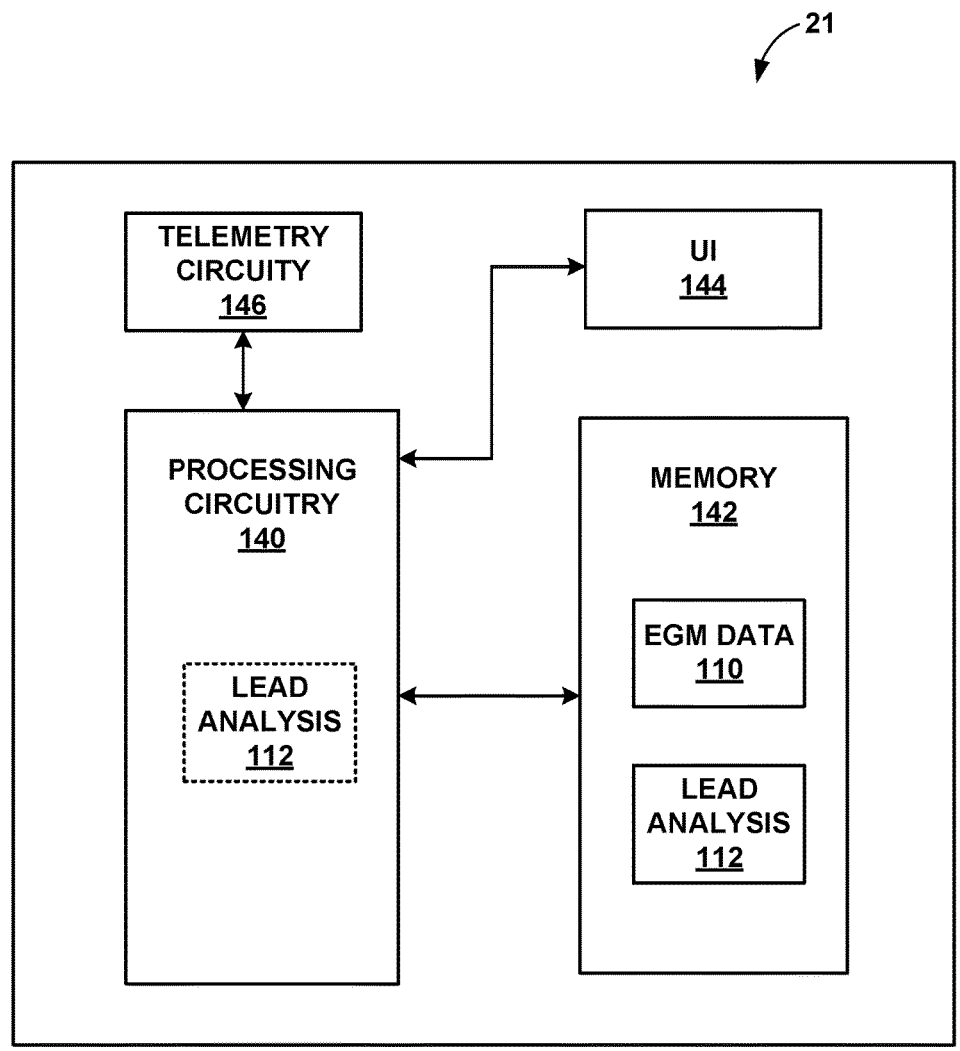
FIG. 6 is a functional block diagram illustrating an example configuration of the external device of FIG. 1 in accordance with one or more aspects of the present disclosure.

FIG. 6 is a functional block diagram of an example configuration of external device 21. In the example of FIG. 6, external device 21 includes processing circuitry 140, memory 142, user interface (UI) 144, and telemetry circuitry 146. External device 21 may be a dedicated hardware device with dedicated software for the programming and/or interrogation of one or more devices within cardiac system 8, including either IPD 16 or IMD 30. Alternatively, external device 21 may be an off-the-shelf computing device, e.g., running an application that enables external device 21 to program and/or interrogate devices within cardiac system 8.

In some examples, a clinician or user uses external device 21 to select or program values for operational parameters of devices within cardiac system 8, e.g., for cardiac sensing, therapy delivery, and disabling and/or enabling IPD 16. In some examples, a clinician uses external device 21 to receive data collected by devices within system 8, such as information about the condition of ICD system 30, including information relating to remaining battery life. External device 21 may also receive data from IPD 16, including whether it delivery of ATP is currently enabled or not. External device 21 may also receive other operational and performance data of devices within cardiac system 8.

The user may interact with external device 21 via UI 144, which may include a display to present a graphical user interface to a user, and a keypad or another mechanism for receiving input from a user. External device 21 may communicate wirelessly with one or more devices within system 8 using telemetry circuitry 146, which may be configured for RF communication with communication circuitry 94 of IPD 16 or communication circuitry 80 of ICD 30. Any appropriate communication protocols beyond RF communication may be used.

Processing circuitry 140 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 106 may include multiple components, such as any combination of one or more microprocessors, one or more DSPs, one or more ASICs, or one or more FPGAs, as well as other discrete or integrated logic circuitry, and/or analog circuitry.

Memory 142 may store program instructions, which may include one or more program modules, which are executable by processing circuitry 140. When executed by processing circuitry 140, such program instructions may cause processing circuitry 140 and external device 21 to provide the functionality ascribed to them herein. The program instructions may be embodied in software, firmware and/or RAMware. Memory 142 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

A clinician may use external device 21 in FIG. 6 to communicate with IPD 16, and thereby enable or disable delivery of ATP therapy in accordance with one or more aspects of the present disclosure. As described below, a clinician may also perform an assessment of devices within cardiac system 8 and use external device 21 to modify or update parameters stored within IPD 16 or other devices within cardiac system 8.

Figure 7:
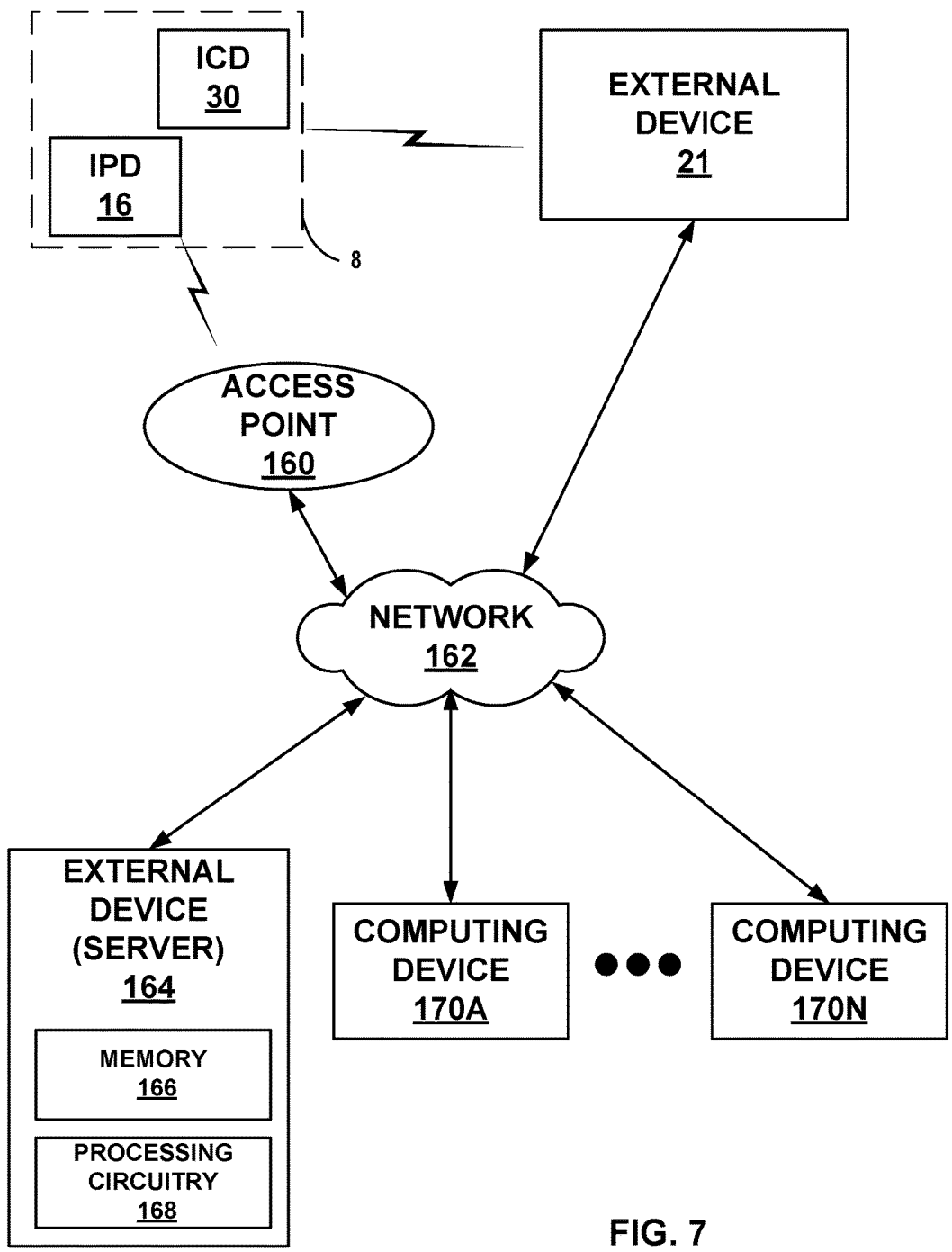
FIG. 7 is a functional block diagram illustrating an example network including the external device of FIG. 1 in accordance with one or more aspects of the present disclosure.

FIG. 7 is a functional block diagram illustrating an example system that includes external computing devices, such as a server 164 and one or more other computing devices 170A-170N, that are coupled to devices within cardiac system 8 (including IPD 16 and ICD system 30) and external device 21 via a network 162. In this example, IPD 16 may use communication circuitry 94 to, e.g., at different times and/or in different locations or settings, communicate with external device 21 via a first wireless connection, and to communicate with an access point 160 via a second wireless connection. Similarly, ICD system 30 may use communication circuitry 80 to, e.g., at different times and/or in different locations or settings, communicate with external device 21 via a first wireless connection, and to communicate with an access point 160 via a second wireless connection. In the example of FIG. 7, access point 160, external device 21, server 164, and computing devices 170A-170N are interconnected, and able to communicate with each other, through network 162.

Access point 160 may comprise a device that connects to network 162 via any of a variety of connections, such as telephone dial-up, digital subscriber line (DSL), or cable modem connections. In other examples, access point 160 may be coupled to network 162 through different forms of connections, including wired or wireless connections. In some examples, access point 160 may be co-located with patient 14. Access point 160 may interrogate devices within the cardiac system 8, e.g., periodically or in response to a command from patient 14 or network 162, to retrieve information such as operational data from devices within cardiac system 8. Access point 160 may provide the retrieved data to server 164 via network 162. In accordance with one or more aspects of the present disclosure, a clinician may use external device 21 in FIG. 7 to communicate with IPD 16, and thereby enable or disable delivery of ATP therapy, and in some examples, modify or update parameters stored within IPD 16 or other devices within cardiac system 8

In some cases, server 164 may be configured to provide a secure storage site for data that has been collected from one or more devices within cardiac system 8 and/or external device 21, such as the Internet. In some cases, server 164 may assemble data in web pages or other documents for viewing by trained professionals, such as clinicians, via computing devices 170A-170N. The illustrated system of FIG. 7 may be implemented, in some aspects, with general network technology and functionality similar to that provided by the Medtronic CareLink® Network developed by Medtronic plc, of Dublin, Ireland.

Figure 8:
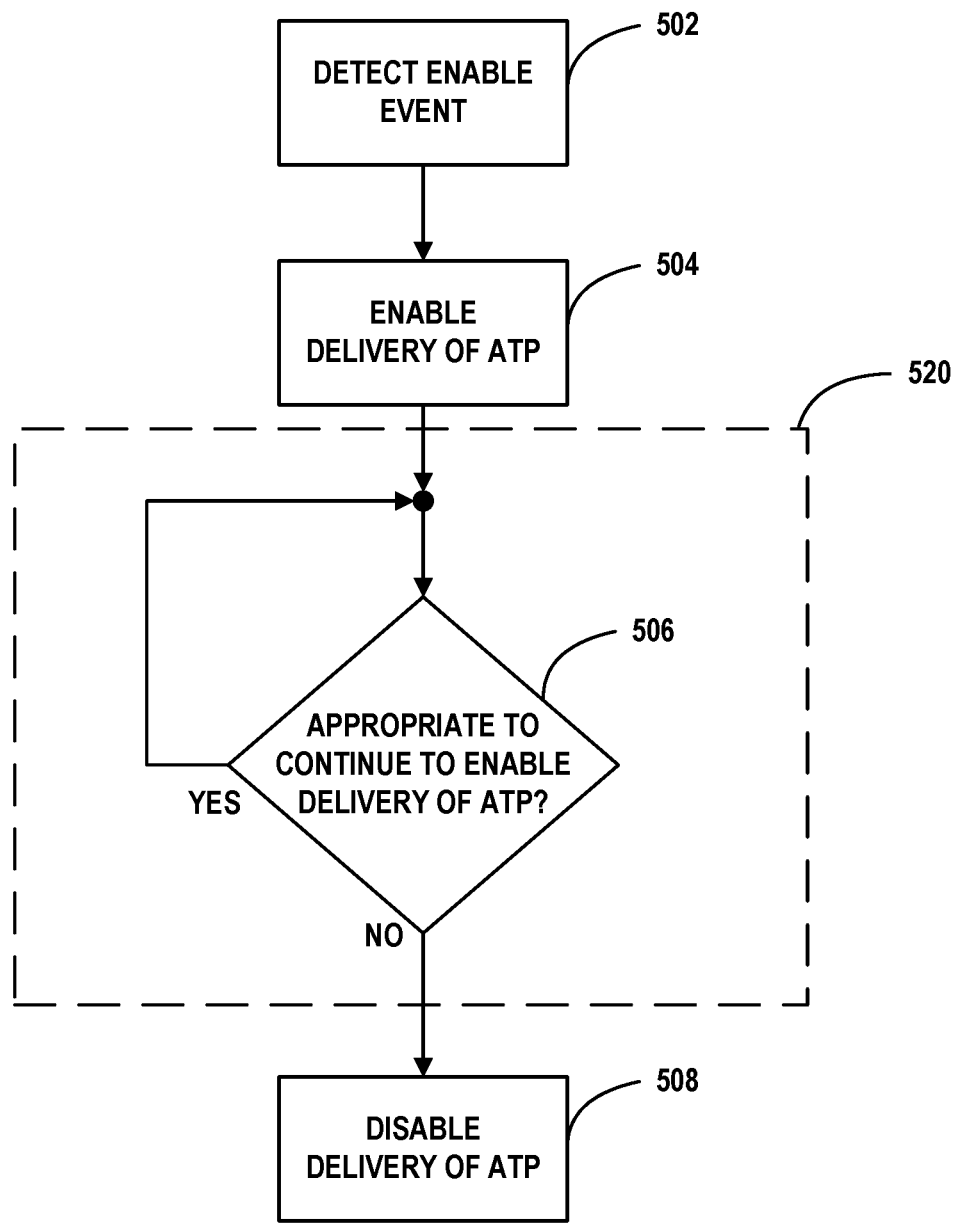
FIG. 8 is a flow diagram illustrating example operations of the example IPD of FIG. 1 and FIG. 4 in accordance with one or more aspects of the present disclosure.

FIG. 8 is a flow diagram illustrating an example process of a system in accordance with one or more aspects of the present disclosure. For purposes of illustration, FIG. 8 is described below within the context of operations performed by IPD 16 of FIG. 1 and FIG. 4, but the operations illustrated by the example of FIG. 8 may be performed by any medical device configured to deliver ATP. FIG. 8 illustrates an example process for enabling and disabling delivery of ATP therapy in an example IPD 16. In the example described in connection with FIG. 8, the example IPD 16 may have capabilities for delivering ATP therapy, but might not have capabilities for delivering an anti-tachyarrhythmia shock (HV shock).

In FIG. 8, processing circuitry 90 within IPD 16 may detect an enable event (502). IPD 16 may detect an enable event as a result of initialization of IPD 16 or as a result of a power-on cycle. For instance, processing circuitry 90 may detect an enable event occurring when power is supplied to IPD 16, which may happen before, during, or after IPD 16 is implanted in patient 14. In other examples, processing circuitry 90 may detect an enable event based on input from sensing circuitry 98, signal generation circuitry 96, shock detection circuitry 99, or activity sensor 100. In other examples, an enable event may be detected based on logic within processing circuitry 90 or based on processing circuitry 90 executing instructions stored in memory 92.

In still further examples, communication circuitry 94 within IPD 16 may detect input or a signal from another device, and may output an indication of an enable event to processing circuitry 90, which may determine, based on the indication of the enable event, that an enable event has been received. In such examples, the signal may originate from an internal device or an external device that may transmit the signal through wireless telemetry or through any appropriate communication technique. In some examples, the signal may originate from an internal device, such as ICD system 30. In other examples, the signal may also originate from an external device, such as external device 21 operated by a clinician or another person, which may include patient 14. In still further examples, the signal may also originate from external device 21 automatically or from another device configured to determine appropriate circumstances for sending an enable signal to IPD 16.

Responsive to detecting an enable event, processing circuitry 90 within IPD 16 may enable delivery of anti-tachyarrhythmia pacing (ATP) therapy (504), which may thereafter result in IPD 16 delivering pacing signals to heart 26 when ATP therapy may be considered appropriate. To cause ATP therapies to be enabled, processing circuitry 90 may in some examples output to signal generation circuitry 96 information that causes signal generation circuitry 96 to enable delivery of ATP, or in other examples, processing circuitry 90 may control signal generation circuitry 96 in a way that results in enabling delivery of ATP. In accordance with one or more aspects of the present disclosure, enabling delivery of ATP may allow ATP therapy to be delivered during a tachycardia episode.

After enabling delivery of ATP therapy, IPD 16 may determine whether it is appropriate for delivery of ATP to continue to be enabled (506). As described above, it may be appropriate for IPD 16 to refrain from or disable delivery of ATP therapy in some cases, such as when no device is considered available to deliver an HV shock. In accordance with one or more aspects of the present disclosure, IPD 16 may determine whether to disable ATP by evaluating whether another device may be available to deliver an HV shock. To perform this evaluation, processing circuitry 90 within IPD 16 may execute instructions stored on memory 92 and may process available information relevant to such an evaluation, which may include information relating to the capabilities and availability of devices in cardiac system 8. Such available information may be derived from communication circuitry 94 detecting direct or broadcast communications that may originate from devices within cardiac system 8. Such available information may also include information derived from communication circuitry 94 detecting direct or broadcast communications that may originate from external devices (e.g., devices not included in cardiac system 8). Such external devices may include external device 21, which may be operated by a clinician or by patient 14 to transmit a signal communicating information to IPD 16. In still other examples, available information may include information received by processing circuitry 90 from signal generation circuitry 96, sensing circuitry 98, shock detection circuitry 99, or activity sensor 100, and may further include information stored in memory 92.

In some examples, as long as IPD 16, or processing circuitry 90 within IPD 16, determines that a device capable of delivering an HV shock can be considered available, delivery of ATP may remain enabled. However, responsive to a determination made by IPD 16 (or processing circuitry 90 within IPD 16) that no HV backup device can be considered available (NO path from 506), IPD 16 may, in some examples, disable delivery of ATP (508). Disabling delivery of ATP may include processing circuitry 90 outputting to signal generation circuitry 96 information that causes signal generation circuitry 96 to disable delivery of ATP, or in other examples, may include processing circuitry 90 controlling signal generation circuitry 96 in such a way that results in disabling delivery of ATP. In accordance with one or more aspects of the present disclosure, disabling ATP may prevent delivery of ATP when an HV backup device is not available.

The determination made at 506 (within sub-process 520), which in some examples may include assessing whether an HV backup device can be considered available, may not always be accurate. In some examples, which may include when IPD 16 and ICD system 30 may be operating independently and might not be in communication with each other, IPD 16 might not be able to make an accurate determination (or a determination having a high degree of certainty), whether ICD system 30 is available as an HV backup device. For example, in some situations, IPD 16 may determine at 506 that an HV backup device is not considered available to deliver an HV shock, when in reality, one or more HV backup devices may in fact be available to deliver an HV shock if appropriate. When this inaccurate assessment is made, delivery of ATP may be disabled, even though an HV backup device is available to deliver an HV shock. Similarly, IPD 16 may determine at 506 that an HV backup device is considered available, when in reality, no device can be relied upon to deliver an HV shock, which may result in IPD 16 continuing to enable delivery of ATP therapy, even though no HV backup device is available to deliver an HV shock. However, despite the potential for inaccurate assessments by IPD 16, including inaccurate assessments as to the availability of an HV backup device, such assessments may still be sufficiently accurate to improve cardiac therapy significantly, particularly where the limitations of IPD 16 in making accurate assessments are understood and addressed.

Figure 9:
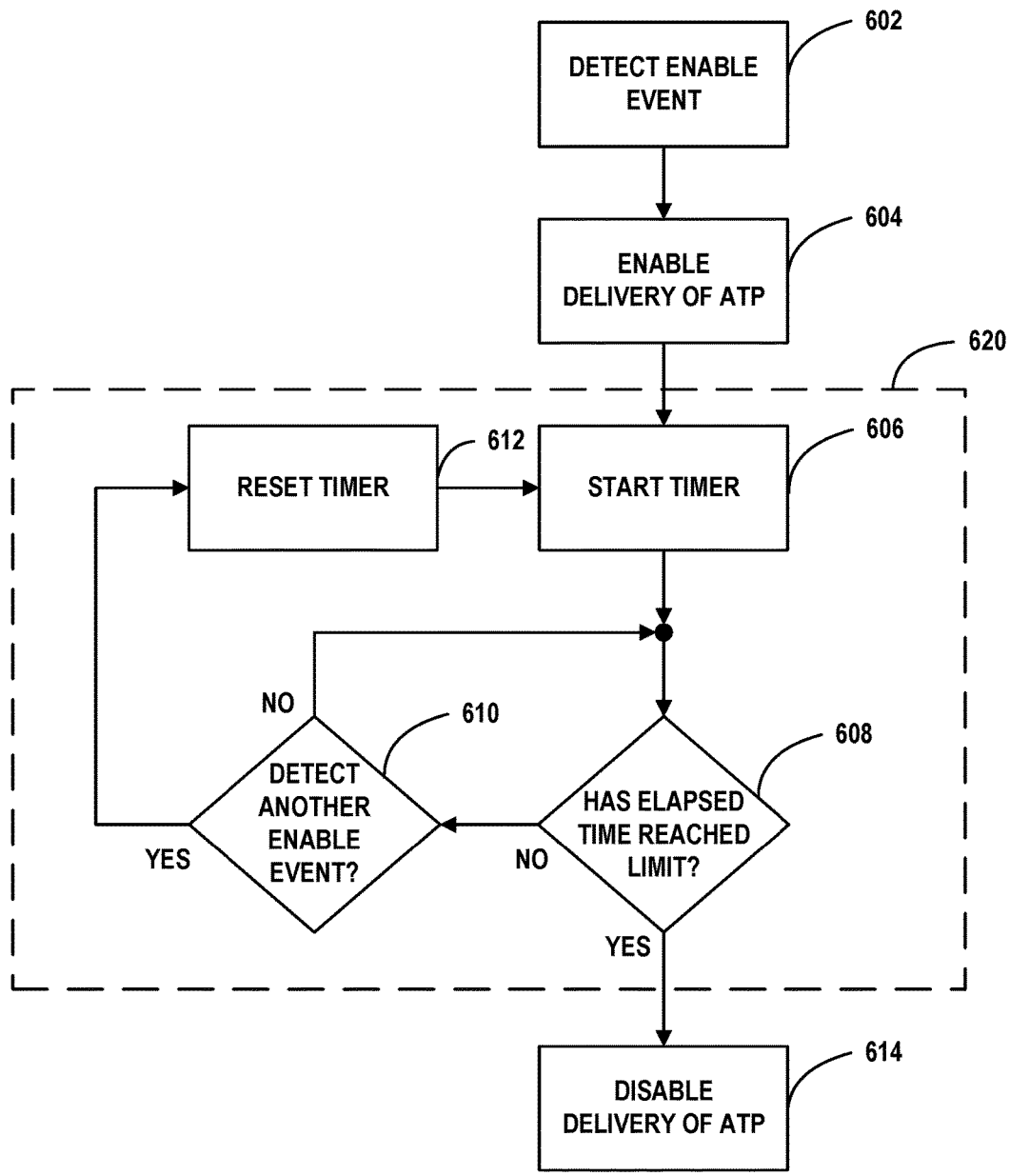
FIG. 9 is a flow diagram illustrating example operations of the example IPD of FIG. 1 and FIG. 4 in accordance with one or more aspects of the present disclosure.

FIG. 9 is a flow diagram illustrating an example process of a system in accordance with one or more aspects of the present disclosure. For purposes of illustration, FIG. 9 is described below within the context of operations performed by IPD 16 of FIG. 1 and FIG. 4. FIG. 9 illustrates an example process for enabling and disabling delivery of ATP therapy in an example IPD 16. In the example described in connection with FIG. 9, the example IPD 16 may have capabilities for delivering ATP therapy, but might not have capabilities for delivering an anti-tachyarrhythmia shock (HV shock).

In the example of FIG. 9, a timer may be used in making an assessment of whether an HV backup device is considered available to deliver an HV shock if appropriate. In a system such as that of FIG. 1, a clinician may make an initial or periodic determination of whether a device, such as ICD system 30, is capable of delivering an HV shock. The clinician may make this determination based on an assessment of ICD system 30, which may include evaluating the age, condition, or battery life remaining in ICD 9 of ICD system 30. Using this information, the clinician may send a signal to IPD 16, and responsive to this signal, IPD 16 may determine how long it might be able to rely on ICD system 30 to serve as an HV backup device. The signal sent by the clinician to IPD 16 may include information including a specific amount of time that ICD system 30 can be relied upon, based on the clinician's assessment. In other examples, the signal may include information that processing circuitry 90 within IPD 16 can use to determine an appropriate amount of time during which ICD system 30 can be relied upon as an HV backup device capable of delivering an HV shock. The clinician may make this determination periodically, and may send additional signals to IPD 16 following subsequent determinations. Although certain aspects of FIG. 9 may be described in terms of a person such as a clinician performing certain operations, in other examples, another person, including patient 14, may perform such operations. In still other examples, such operations may be performed by a computer, appliance, or other device, which may operate autonomously, or may be operated by a person.

With reference to FIG. 9, processing circuitry 90 within IPD 16 may detect an enable event (602). As described above, the enable event may be detected by IPD 16 following a signal sent by a clinician based on an assessment of ICD system 30. In other examples, the enable event may include any of the example enable events described in connection with FIG. 8, including a signal that may originate from an internal device or an external device, or based on input from circuitry or modules within IPD 16. Responsive to detecting the enable event, processing circuitry 90 within IPD 16 may enable delivery of ATP therapy (604), such as in the manner described in connection with FIG. 8.

After enabling delivery of ATP therapy, IPD 16 may determine whether another device capable of delivering an HV shock, such as ICD system 30, is considered available. The process for making this determination may, in some examples, include the sub-process 620 in FIG. 9, although in other examples, the process for making this determination may include more operations, less operations, or different operations. In some examples, the sub-process 620 may correspond to the determination made in sub-process 520 in FIG. 8.

Still referring to FIG. 9, processing circuitry 90 within IPD 16 may start a timer (606) that may be used in making a determination of whether an HV backup device capable of delivering an HV shock is considered available. Processing circuitry 90 may monitor the timer and determine whether the time elapsed has reached a time limit (608). In some examples, the time limit may be based on input received by processing circuitry 90 from communication circuitry 94. In some examples, communication circuitry 94 may detect a signal corresponding to an enable event, such as a signal sent by a clinician, and output to processing circuitry 90 an indication of the signal received. In other examples, the time limit may be based on other information available to processing circuitry 90, including input from signal generation circuitry 96, sensing circuitry 98, shock detection circuitry 99, activity sensor 100, or memory 92.

Before the time limit is reached, IPD 16 may also detect another enable event (610), which may cause processing circuitry 90 to reset the timer (612) so that in some examples, the timer starts again with zero elapsed time. Detecting an enable event in such a situation may be the result of communication circuitry 94 receiving a signal from external device 21 operated by a clinician during a clinician's periodic assessment of HV backup devices in cardiac system 8, such as ICD system 30.

Until processing circuitry 90 detects that the timer has reached the time limit, delivery of ATP may continue to be enabled. In some examples, the time limit may be chosen to provide a higher degree of certainty that an HV backup device is available until the timer reaches the time limit. This may include setting a time limit relatively low, so that ICD system 30 is not likely to fail due to limited battery life or other issues before the time limit is reached. Where a new assessment of the capabilities of ICD system 30 can be made frequently, using a time limit set relatively low may be appropriate in some examples. In other examples, the time limit may be fixed, or may change in response to processing circuitry 90 receiving input from signal generation circuitry 96, sensing circuitry 98, shock detection circuitry 99, activity sensor 100, or memory 92.

If processing circuitry 90 detects that the elapsed time has reached the limit, IPD 16 may disable delivery of ATP. As described in connection with FIG. 8, disabling delivery of ATP may, in some examples, include processing circuitry 90 outputting to signal generation circuitry 96 information that causes signal generation circuitry 96 to disable delivery of ATP, or in other examples, may include processing circuitry 90 controlling signal generation circuitry 96 in such a way that results in disabling delivery of ATP. In accordance with one or more aspects of the present disclosure, disabling ATP may prevent delivery of ATP when an HV backup device is not available.

Figure 10A:
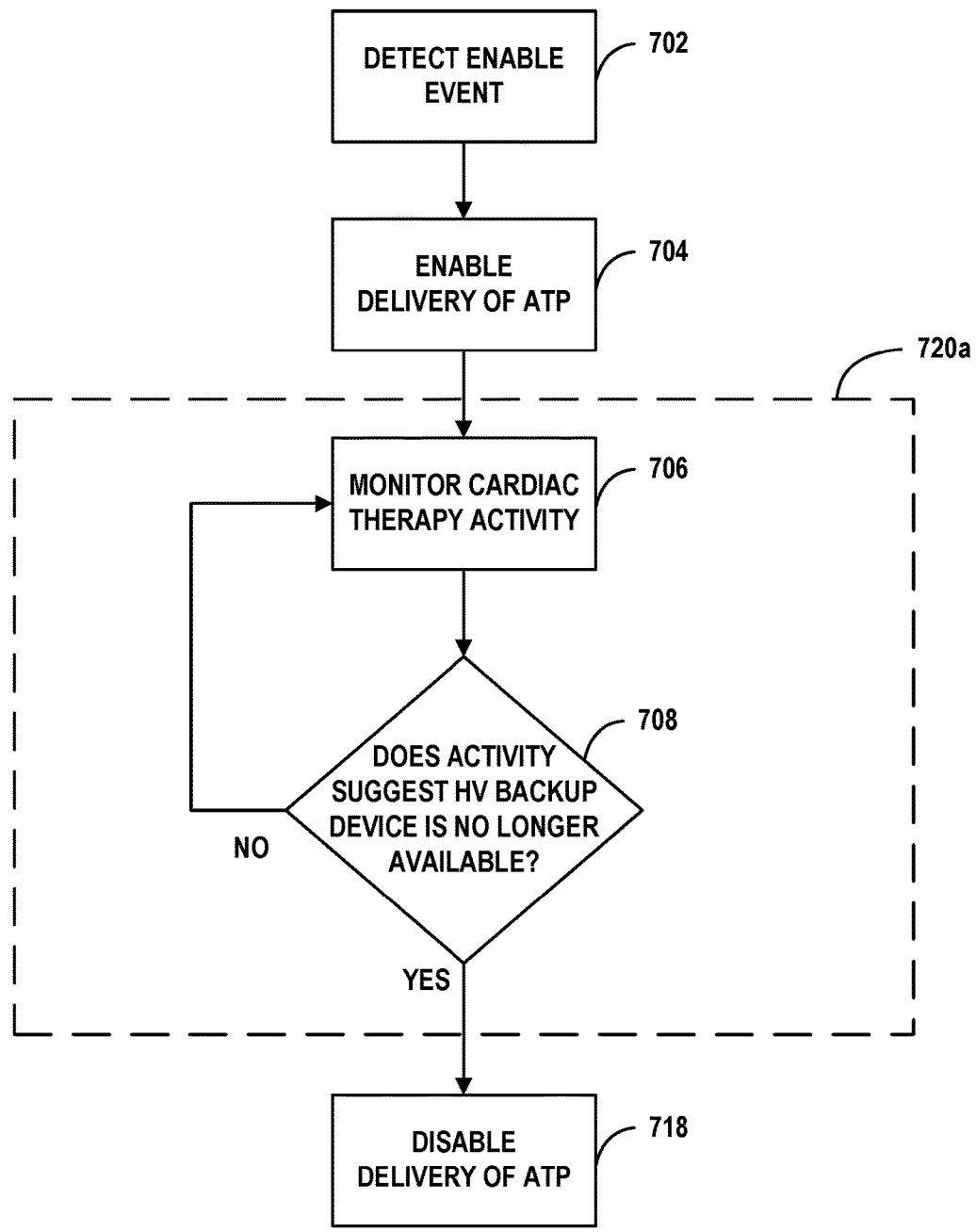
FIG. 10A is a flow diagram illustrating example operations of the example IPD of FIG. 1 and FIG. 4 in accordance with one or more aspects of the present disclosure.
Figure 10B:
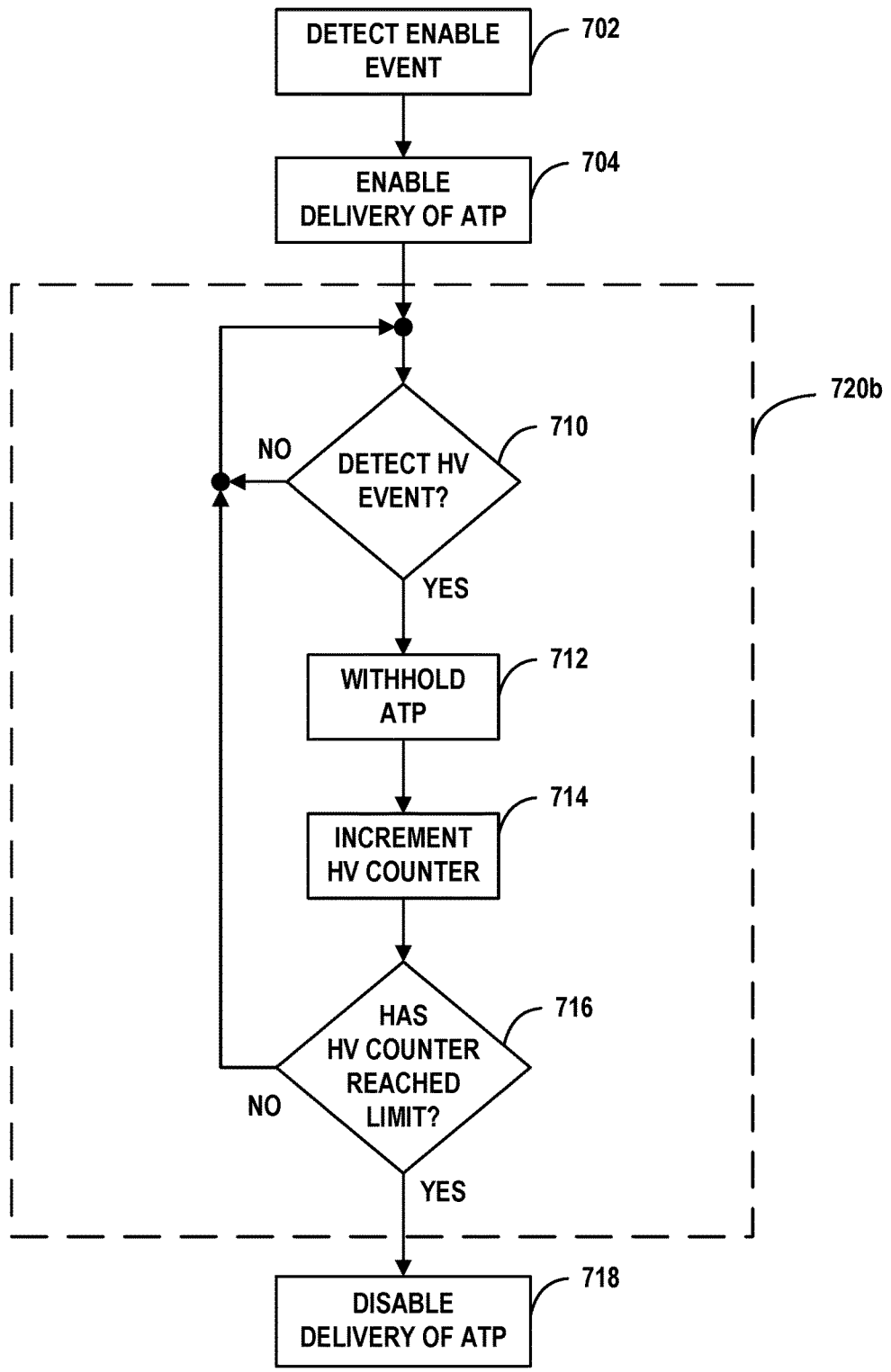
FIG. 10B is a flow diagram illustrating example operations of the example IPD of FIG. 1 and FIG. 4 in accordance with one or more aspects of the present disclosure.

FIG. 10A and FIG. 10B are flow diagrams illustrating example processes of a system in accordance with one or more aspects of the present disclosure. For purposes of illustration, FIG. 10A and FIG. 10B are described below within the context of operations performed by IPD 16 of FIG. 1 and FIG. 4. FIG. 10A and FIG. 10B illustrate example processes for enabling and disabling delivery of ATP therapy in an example IPD 16. In the examples described in connection with FIG. 10A and FIG. 10B, the example IPD 16 may have capabilities for delivering ATP therapy, but might not have capabilities for delivering an anti-tachyarrhythmia shock (HV shock).

In the examples of FIG. 10A and FIG. 10B, IPD 16 may monitor cardiac therapy activity of cardiac system 8 to make an assessment of whether an HV backup device is considered available to deliver an HV shock if appropriate. In example systems such as those described in connection with FIG. 10A and FIG. 10B, IPD 16 may independently monitor cardiac therapy activity, including therapy delivered by ICD system 30 or by any other device included within cardiac system 8. Based on information determined from such monitoring, IPD 16 may be able to determine whether an HV backup device is considered available.

With reference to FIG. 10A, processing circuitry 90 within IPD 16 may detect an enable event (702). The enable event may include any of the examples described in connection with FIG. 8 or FIG. 9, including a signal that may originate from an internal device or an external device, or based on input to processing circuitry 90 from circuitry or modules within IPD 16. Responsive to detecting the enable event, processing circuitry 90 within IPD 16 may enable delivery of ATP therapy (704), as described in connection with FIG. 8 and FIG. 9.

After enabling delivery of ATP therapy, IPD 16 may determine whether another device capable of delivering an HV shock, such as ICD system 30, is considered available. The process for making this determination may, in some examples, include the sub-process 720 in FIG. 10A, although in other examples, the process for making this determination may include more operations, less operations, or different operations. In some examples, the sub-process 720*a* may correspond to sub-process 520 in FIG. 8.

Still referring to FIG. 10A, IPD 16 monitors cardiac therapy of cardiac system 8 (706). This may include sensing circuitry 98 within IPD 16 detecting signals or voltage levels via electrode 52 and electrode 60, such as might occur if ICD system 30 were to deliver an HV shock during the course of delivering cardiac therapy to patient 14. Sensing circuitry 98 may also monitor other activity of cardiac system 8 by detecting signals or voltage levels via electrode 52 and electrode 60.

Responsive to detecting such signals or voltage levels, sensing circuitry 98 may output to shock detection circuitry 99 an indication of signals sensed at electrode 52 and electrode 60. Also responsive to such signals, sensing circuitry 98 may output to processing circuitry 90 an indication of signals sensed at electrode 52 and electrode 60. Shock detection circuitry 99 may also provide input to processing circuitry 90 that includes information about the input from m98 based on the signals sensed at electrode 52 and electrode 60. Shock detection circuitry 99 may be configured to detect cardiac therapy activity and output to processing circuitry 90 information about the detected cardiac therapy activity. Responsive to receiving an indication of signals sensed, and/or responsive to receiving input from sensing circuitry 98 or shock detection circuitry 99, processing circuitry 90 may determine information about cardiac therapy activity in cardiac system 8. Processing circuitry 90 uses this information to determine whether an HV backup device, such as ICD system 30, is available (or no longer available) to deliver an HV shock (708). In this way, IPD 16 may continue to monitor cardiac therapy activity of cardiac system 8 (706) in the example shown. If processing circuitry 90 within IPD 16 determines that the monitored cardiac therapy activity suggests that the HV backup device, such as ICD system 30, may no longer be available, IPD 16 may disable delivery of ATP (718), which may include processing circuitry 90 within IPD 16 disabling delivery of ATP as previously described in connection with FIG. 8 or FIG. 9, and in accordance with one or more aspects of this disclosure.

Referring now to FIG. 10B, sub-process 720*a* in FIG. 10A has been replaced in FIG. 10B with an example sub-process 720*b* that illustrates IPD 16 monitoring cardiac activity for one or more specific events. In the example of FIG. 10B, IPD 16 monitors for HV events in cardiac system 8, which may be delivered by ICD system 30. In some examples, such as when ICD 9 within ICD system 30 is powered by a battery, ICD system 30 may have the capability of delivering only a limited number of HV shocks, since each HV shock may diminish remaining battery life. If ICD system 30 delivers a sufficient number of HV shocks, ICD system 30 may reach a state where it no longer has adequate battery power to reliably deliver another HV shock. If ICD system 30 is unable to deliver an HV shock, it may be appropriate to disable delivery of ATP therapy.

In the example of FIG. 10B, each time IPD 16 detects an HV event (710), processing circuitry 90 within IPD 16 may increment a counter (712) within processing circuitry 90 to keep track of information relevant to battery life for ICD system 30. The counter may, in some examples, be implemented as part of the timing and control module of processing circuitry 90. Until processing circuitry 90 detects that a threshold number of HV events have been detected, delivery of ATP may continue to be enabled (NO path from 716). In some examples, the threshold number of HV events may be a predetermined number, which may be based on the type or capabilities of the HV backup device being monitored. Once a sufficient number of HV events are detected by processing circuitry 90, processing circuitry 90 may determine that ICD system 30 no longer has sufficient battery life to be relied upon as an HV backup device (716). Responsive to such a determination, IPD 16 may disable delivery of ATP (718).

In other examples, processing circuitry 90 may use information beyond simply a count of HV events to determine whether ICD system 30 may or may not have sufficient battery life to be relied upon as an HV backup device. Such information may include information about the voltage levels or waveform associated with HV events detected in the system, or information about the time period in which HV events were detected, or information about other events detected in the system.

Also, in some examples, when IPD 16 detects delivery of an HV shock, IPD 16 may adjust cardiac therapy following the delivery of the HV shock, such as by withholding ATP therapy (712). Withholding ATP delivery in this manner may be temporary in some examples, and may not disable delivery of ATP therapy. In other examples, IPD 16 may deliver post-shock therapy after detecting an HV event.

In the example of FIG. 10B, IPD 16 may monitor for HV events in cardiac system 8 in an attempt to determine capabilities and remaining battery life of ICD system 30, but IPD 16 might not receive any direct communications from ICD system 30. In fact, in some examples, IPD 16 might not be able to verify or confirm that any given HV shock was in fact delivered by ICD system 30, as opposed to another device. But such verification or confirmation may not be necessary. For example, in a system where it is known that only one device has the capability for delivering an HV shock, if an HV shock is detected by IPD 16, processing circuitry 90 within IPD 16 might justifiably conclude that the HV shock was delivered by ICD system 30.

Further, even in a system where there may be more than one possible source for an HV shock, processing circuitry 90 may be able to determine that some percentage of any HV shocks detected by IPD 16 were actually delivered by ICD system 30. Processing circuitry 90 may make such a determination based on input, received by processing circuitry 90, that includes information about cardiac system 8 or devices included in cardiac system 8. Processing circuitry 90 may also make such a determination based on detected cardiac therapy activity, which may include information detected by sensing circuitry 98 that enables processing circuitry 90 to distinguish between HV shocks delivered by ICD system 30 and those delivered by another device.

Accordingly, in some examples where formal or informal communication between IPD 16 and other devices within a system is limited, IPD 16 may still be able to monitor cardiac therapy and derive useful information about the activity or condition of other devices within the system. Such information may be sufficient to enable processing circuitry 90 within IPD 16 to make sufficiently accurate determinations about remaining battery life for ICD system 30 or another potential backup HV device.

Figure 11:
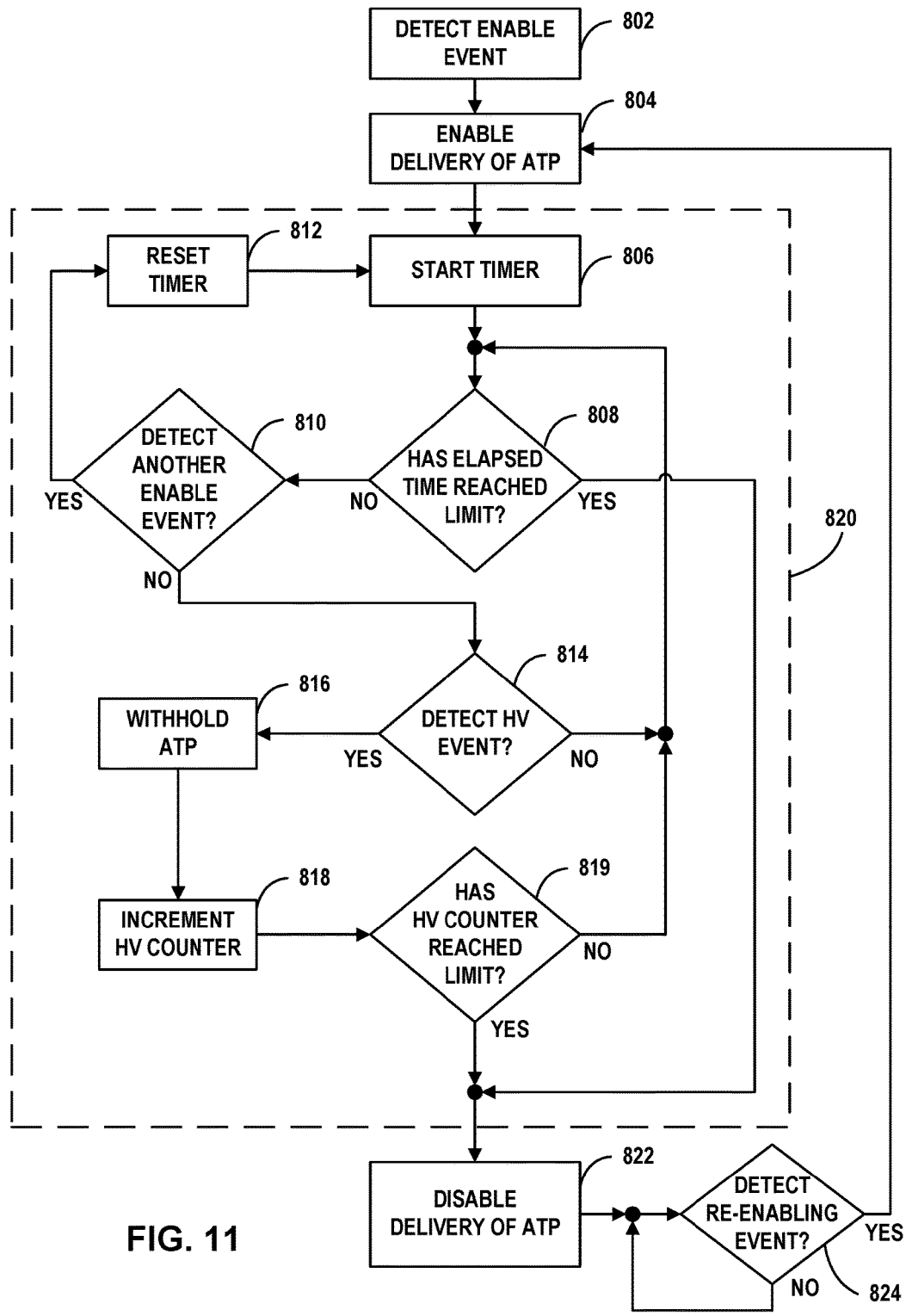
FIG. 11 is a flow diagram illustrating example operations of the example IPD of FIG. 1 and FIG. 4 in accordance with one or more aspects of the present disclosure.

FIG. 11 is a flow diagram illustrating an example process of a system in accordance with one or more aspects of the present disclosure. For purposes of illustration, FIG. 11 is described below within the context of operations performed by IPD 16 of FIG. 1 and FIG. 4. FIG. 11 illustrates an example process for enabling and disabling delivery of ATP therapy in an example IPD 16. In the example described in connection with FIG. 11, the example IPD 16 may have capabilities for delivering ATP therapy, but might not have capabilities for delivering an anti-tachyarrhythmia shock (HV shock).

With reference to FIG. 11, processing circuitry 90 within IPD 16 may detect an enable event (802), and responsive to detecting the enable event, processing circuitry 90 within IPD 16 may enable delivery of ATP therapy (804). In the example of FIG. 11, after enabling delivery of ATP, IPD 16 may monitor cardiac therapy activity and may also employs a timer to determine whether an HV backup device should be considered available to deliver an HV shock if appropriate. As long as an HV backup device is considered available, ATP therapy may continue to be enabled; otherwise, ATP therapy may be disabled.

At 806 in FIG. 11, processing circuitry 90 within IPD 16 may start a timer and monitor the elapsed time until the elapsed time reaches the time limit (808). If IPD 16 detects another enable event (810) before the timer reaches the time limit, the timer may be reset so that in some examples, the elapsed time is reset to zero (812). IPD 16 may also monitor for HV events in cardiac system 8 (814). When an HV event is detected (YES path from 814), IPD 16 may withhold ATP therapy in some examples (816). IPD 16 may increment an HV counter when it detects an HV event (818), and IPD 16 may monitor the HV counter to detect whether a limit, which may suggest that an HV backup device can no longer be relied upon, has been reached (819). IPD 16 may continue to monitor elapsed time and HV events until the timer reaches the time limit (YES path from 808), or until the HV counter has reached its limit (YES path from 819). If IPD 16 detects either condition, IPD 16 may disable delivery of ATP therapy.

In some examples, IPD 16 may detect a re-enabling event, which may cause IPD 16 to enable delivery of ATP therapy (YES path from 824). In some examples, IPD 16 may detect a re-enabling event as the result of a clinician sending a signal to IPD 16. In other examples, IPD 16 may detect a re-enabling event as a result of another device, which may include an HV backup device, sending a signal to IPD 16. In still further examples, IPD 16 may detect a re-enable event based cardiac therapy activity detected by IPD 16, or based on input from sensing circuitry 98, signal generation circuitry 96, shock detection circuitry 99, or activity sensor 100. In still other examples, a re-enable event may be detected based on logic within processing circuitry 90 or based on processing circuitry 90 executing instructions stored in memory 92.

In some examples, memory 92 may store parameters that may be used by IPD 16 in a process such as that described in connection with FIG. 11. Such parameters may include, but are not limited to, the amount of time elapsed, information relating to the timer limit, parameters for determining how to adjust the timer limit based on cardiac therapy detected, the number of HV shocks detected, and information relating to a any limit on HV shocks.

Figure 12:
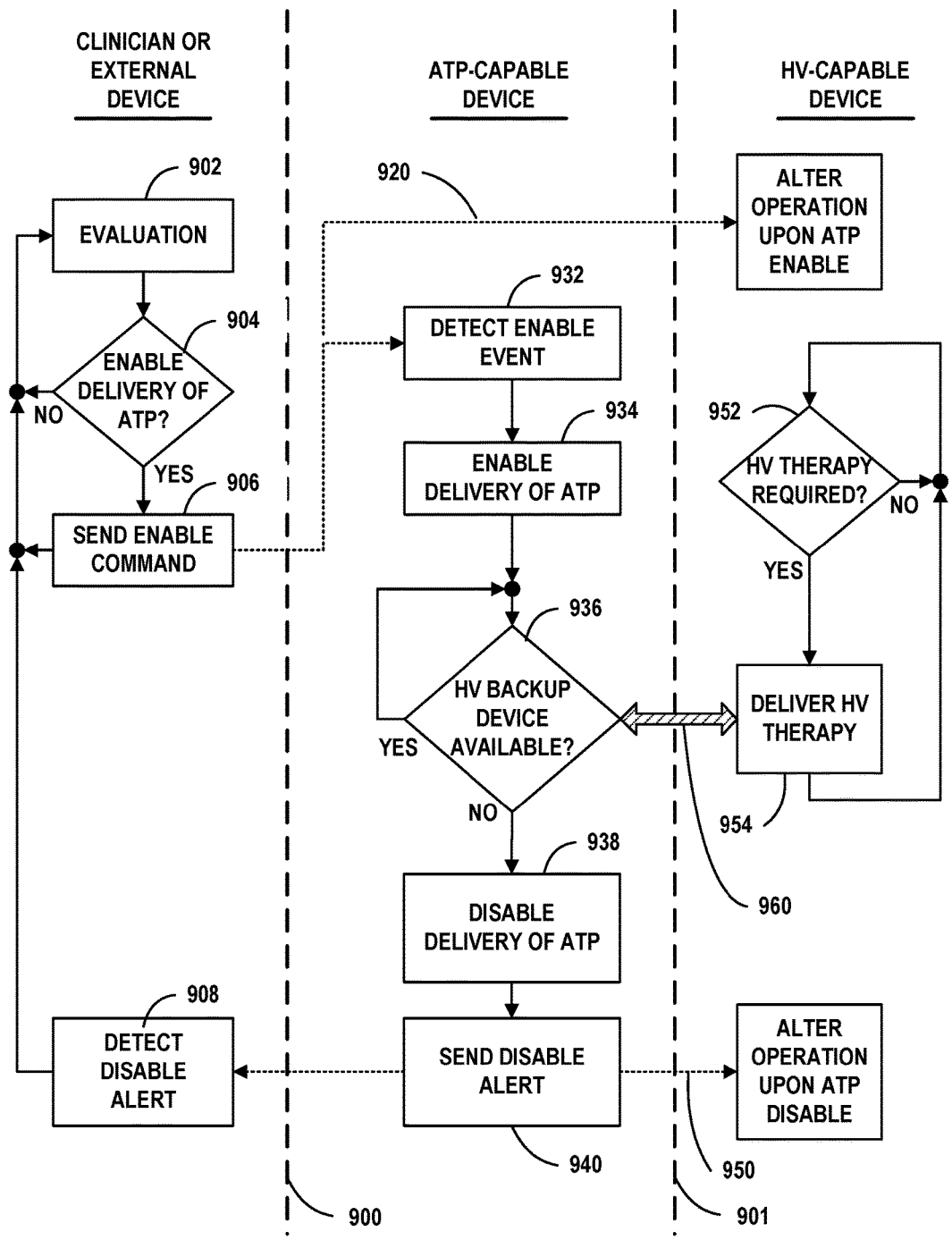
FIG. 12 is a flow diagram illustrating example operations of the example medical device system of FIG. 1 in accordance with one or more aspects of the present disclosure.

FIG. 12 is a flow diagram illustrating an example process of a system in accordance with one or more aspects of the present disclosure. For purposes of illustration, FIG. 12 is described from three different perspectives, each relating to an example system such as cardiac system 8 shown in FIG. 1. The first perspective (along the left side of line 900 in FIG. 12) may be that of a clinician that may operate external device 21, which may be used to send information to, or receive information from, an ATP-capable device, such as IPD 16. External device 21 may also communicate with other devices within cardiac system 8. The second perspective (between lines 900 and 901 in FIG. 12) may be that of an ATP capable device, such as IPD 16. The third perspective (along the right side of line 901 in FIG. 12) may be that of an HV capable device, or HV backup device, such as ICD system 30 including ICD 9. FIG. 12 illustrates an example process for performing operations including enabling and disabling delivery of ATP therapy in an example cardiac system 8. In the example described in connection with FIG. 12, the example IPD 16 may have capabilities for delivering ATP therapy, but might not have capabilities for delivering an anti-tachyarrhythmia shock (HV shock). Further, the example ICD system 30 may have capabilities for delivering an HV shock, but might not have capabilities for delivering ATP therapy.

Referring to FIG. 12, a clinician may perform an evaluation (902) of patient 14 and/or cardiac system 8 to determine whether it is appropriate to enable delivery of ATP in IPD 16 (904). The clinician may perform such an evaluation, and if delivery of ATP should be enabled, external device 21 may send an enable command to IPD 16 (906). Clinicians or other personnel (including patient 14) may periodically perform such assessments or evaluations (902) and when appropriate, use external device 21 or a similar device to send enable or re-enable commands to IPD 16 (906). In some examples, a clinician or external device 21 may perform an evaluation in response to receiving a disable alert from IPD 16 (908).

Referring now to the middle column of FIG. 12, IPD 16 may detect an enable event received from external device 21 (932), and responsive to detecting the enable event, IPD 16 may enable delivery of ATP (934). IPD 16 may then perform operations to determine whether an HV backup device can still be considered available to deliver an HV shock (936). Such operations may be similar to those previously described in connection with sub-processes 520, 620, 720a, 720b, and 820 in FIG. 8, FIG. 9, FIG. 10A, FIG. 10B, and FIG. 11. Delivery of ATP may remain enabled until IPD 16 determines that an HV backup device can no longer be considered available. Responsive to such a determination, IPD 16 may disable delivery of ATP (938). In some examples, IPD 16 may send a disable alert, which may include sending or setting an alert for evaluation by a clinician (940).

Referring now to the right-hand column of FIG. 12, ICD system 30 may operate autonomously until processing circuitry 70 within ICD system 30 determines that HV therapy may be required or desirable (952). Processing circuitry 70 may make this determination based on input from sensing circuitry 78, activity sensor 82, signal generation circuitry 76, communications circuitry 80, or from another source, or based on logic within processing circuitry 70. When appropriate, ICD system 30 may deliver cardiac therapy through signal generation circuitry 76 and/or shock circuitry 75. The cardiac therapy delivered by ICD system 30 may include an HV shock (954). In FIG. 12, arrow 960 may indicate that IPD 16 monitors such therapy and may use information about the monitored therapy to make an assessment at 936.

In some examples, communications circuitry 80 within ICD system 30 may detect an enable command or information about an enable command sent by external device 21 (906 and 920). Responsive to receiving the enable command or information about an enable command, ICD system 30 may alter its operation. See FIG. 12 Similarly, communications circuitry 80 within ICD system 30 may detect a disable alert or information about a disable alert sent by IPD 16 (940 and 950). Responsive to receiving the disable alert or information about the disable alert, ICD system 30 may alter its operation. See FIG. 12

Techniques in accordance with the present disclosure may include disabling delivery of ATP therapy in an otherwise ATP-capable device. A device that is configured to deliver ATP therapy, but that in some circumstances does not deliver ATP therapy, may perform fewer operations and deliver fewer pacing signals to a patient's heart. As a result, such a device may consume less electrical power.

In some examples, the operations shown or described in flow diagrams may be performed in a different order or presented in a different sequence, but still be in accordance with one or more aspects of the present disclosure. Also, while certain operations may be presented in a particular sequence, in other examples, operations may be performed in parallel or substantially parallel, yet still be in accordance with one or more aspects of the present disclosure. Further, a process or technique in accordance with one or more aspects of the present disclosure may be implemented with less than the operations shown or described, and in other examples, such a process may be implemented with more than the operations shown or described.

Any suitable modifications may be made to the processes described herein and any suitable device, processing circuitry, therapy delivery circuitry, and/or electrodes may be used for performing the steps of the methods described herein. The steps the methods may be performed by any suitable number of devices. For example, a processing circuitry of one device may perform some of the steps while a therapy delivery circuitry and/or sensing circuitry of another device may perform other steps of the method, while communication circuitry may allow for communication needed for the processing circuitry to receive information from other devices. This coordination may be performed in any suitable manner according to particular needs.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to ICD system 30, IPD 16, external device 21, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between ICD system 30, IPD 16, and/or external device 21. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

As used herein, the term "circuitry" refers to an application specific integrated circuit (ASIC), an electronic circuit, a processor (shared, dedicated, or group) and memory that execute one or more software or firmware programs, a combinational logic circuit, or other suitable components that provide the described functionality.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described for delivering cardiac stimulation therapies as well as coordinating the operation of various devices within a patient. Any combination of the described operations or functions is contemplated. These and other examples may be within the scope of the following claims.

What is claimed is:

1. A method comprising:
   detecting, by an implantable medical device configured to deliver anti-tachyarrhythmia pacing (ATP) to a heart of a patient, an enable event;
   responsive to detecting the enable event, enabling, by the implantable medical device, the delivery of ATP;
   responsive to detecting the enable event, starting, by the implantable medical device, a timer;
   detecting, by the implantable medical device, a disable event indicating that another implantable medical device cannot be relied upon to deliver an anti-tachyarrhythmia shock, wherein detecting the disable event comprises detecting that the timer has reached a time limit without requiring communication between the implantable medical device and the other implantable medical device; and responsive to detecting the disable event, disabling, by the implantable medical device, delivery of ATP.

2. The method of claim 1, wherein detecting the enable event comprises receiving, by the implantable medical device, an enable signal from an external device via wireless communication.

3. The method of claim 1, wherein the enable event is a first enable event, further comprising:
detecting, by the implantable medical device after starting the timer, a second enable event; and
responsive to detecting the second enable event, restarting, by the implantable medical device, the timer.

4. The method of claim 3,
wherein detecting the second enable event comprises detecting the second enable event after disabling the delivery of ATP,
the method further comprising, responsive to detecting the second enable event, enabling, by the implantable medical device, delivery of ATP.

5. The method of claim 1,
wherein the implantable medical device comprises an intracardiac pacemaker configured for implantation in the heart, and
wherein the other implantable medical device comprises an extracardiovascular implantable cardiac defibrillator configured for extracardiovascular implantation in the patient.

6. The method of claim 1, further comprising:
responsive to detecting the disable event, generating, by the implantable medical device, a disable alert.

7. A method comprising:
detecting, by an implantable medical device configured to deliver anti-tachyarrhythmia pacing (ATP) to a heart of a patient, an enable event;
responsive to detecting the enable event, enabling, by the implantable medical device, the delivery of ATP;
responsive to detecting the enable event, starting, by the implantable medical device, a timer;
detecting, by the implantable medical device, a disable event indicating that another implantable medical device cannot be relied upon to deliver an anti-tachyarrhythmia shock, wherein detecting the disable event comprises detecting that the timer has reached a time limit;
responsive to detecting the disable event, disabling, by the implantable medical device, delivery of ATP;
detecting, by the implantable medical device via a plurality of electrodes, cardiac therapy activity; and
modifying, by the implantable medical device, the timer based on detection of the cardiac therapy activity.

8. The method of claim 7, wherein detecting the enable event comprises detecting, by the implantable medical device, a signal, wherein the signal is generated by the other implantable medical device.

9. The method of claim 8, wherein detecting the enable event comprises detecting the signal via wireless communication.

10. The method of claim 7,
wherein detecting the cardiac therapy activity comprises detecting delivery of one or more anti-tachyarrhythmia shocks, and
wherein modifying the timer comprises shortening the time limit in response to detecting the delivery of the one or more anti-tachyarrhythmia shocks.

11. A method comprising:
detecting, by an implantable medical device configured to deliver anti-tachyarrhythmia pacing (ATP) to a heart of a patient, an enable event;
responsive to detecting the enable event, enabling, by the implantable medical device, the delivery of ATP;
detecting, by the implantable medical device, a disable event indicating that another implantable medical device cannot be relied upon to deliver an anti-tachyarrhythmia shock, wherein detecting the disable event comprises detecting delivery of a threshold number of anti-tachyarrhythmia shocks, thereby suggesting that the other implantable medical device cannot be relied upon to deliver an anti-tachyarrhythmia shock; and
responsive to detecting the disable event, disabling, by the implantable medical device, delivery of ATP.

* * * * *